United States Patent
Hayakawa et al.

(10) Patent No.: US 7,696,487 B2
(45) Date of Patent: Apr. 13, 2010

(54) CIRCUIT PATTERN INSPECTION APPARATUS

(75) Inventors: Koichi Hayakawa, Hitachinaka (JP); Jiro Inoue, Ryugasaki (JP); Masaaki Nojiri, Hitachinaka (JP)

(73) Assignees: Hitachi High-Technologies Corporation, Tokyo (JP); Renesas Technology Corp., Tokyo (JP)

( * ) Notice: Subject to any disclaimer, the term of this patent is extended or adjusted under 35 U.S.C. 154(b) by 373 days.

(21) Appl. No.: 11/594,985

(22) Filed: Nov. 9, 2006

(65) Prior Publication Data

US 2007/0114397 A1    May 24, 2007

(30) Foreign Application Priority Data

Nov. 11, 2005   (JP)   ............................ 2005-327541

(51) Int. Cl.
*G01K 1/08*   (2006.01)
*H01J 3/14*   (2006.01)

(52) U.S. Cl. .................. 250/397; 250/306; 250/307; 250/309; 250/310; 250/311; 356/399; 356/237.1; 356/239.1

(58) Field of Classification Search ............... 250/306, 250/307, 309–311, 397–400, 396 R, 396 ML, 250/491.1, 492.1, 492.2, 492.21, 492.3; 356/237, 356/386, 387, 390, 394, 398, 446, 448, 237.1, 356/239.3, 239.7, 399; 396/398

See application file for complete search history.

(56) References Cited

U.S. PATENT DOCUMENTS

| 4,633,504 A | 12/1986 | Wihl |
| 5,085,517 A | 2/1992 | Chadwick et al. |
| 5,430,548 A * | 7/1995 | Hiroi et al. .................. 356/394 |
| 5,502,306 A | 3/1996 | Meisburger et al. |
| 6,107,637 A * | 8/2000 | Watanabe et al. ......... 250/559.3 |
| 6,157,451 A * | 12/2000 | Mizuno ....................... 356/394 |
| 6,333,510 B1 * | 12/2001 | Watanabe et al. ...... 250/559.27 |

(Continued)

FOREIGN PATENT DOCUMENTS

JP   59-155941   9/1984

(Continued)

OTHER PUBLICATIONS

"Monthly Semiconductor World," Aug. 1995, pp. 96-99.

(Continued)

*Primary Examiner*—Bernard E Souw
(74) *Attorney, Agent, or Firm*—McDermott Will Emery LLP

(57) ABSTRACT

The via chain conduction failure due to non-conduction caused by insufficient etching in a contact plug/via plug forming process can be detected precisely in a short time. For its achievement, a defect is detected at high speed by taking advantage of characteristics of a potential contrast method using a via chain defect inspection structure and an electron beam defect detection apparatus which can perform continuous inspection while changing an inspection direction without rotating a wafer. Accordingly, the capturing efficiency of a critical electric defect and search efficiency of a defect point can be improved.

18 Claims, 19 Drawing Sheets

U.S. PATENT DOCUMENTS

| | | | |
|---|---|---|---|
| 6,381,356 B1 * | 4/2002 | Murakami et al. | 382/141 |
| 6,493,082 B2 * | 12/2002 | Nara et al. | 356/394 |
| 6,903,821 B2 * | 6/2005 | Nara et al. | 356/394 |
| 6,919,577 B2 * | 7/2005 | Watanabe et al. | 250/559.4 |
| 7,095,022 B2 * | 8/2006 | Nakasuji et al. | 250/310 |
| 7,129,485 B2 * | 10/2006 | Nakasuji et al. | 250/310 |
| 7,329,889 B2 * | 2/2008 | Watanabe et al. | 250/559.3 |
| 7,423,267 B2 * | 9/2008 | Nakasuji et al. | 250/310 |
| 2002/0053634 A1 * | 5/2002 | Watanabe et al. | 250/201.2 |
| 2002/0109090 A1 * | 8/2002 | Nakasuji et al. | 250/311 |
| 2002/0113967 A1 * | 8/2002 | Nara et al. | 356/394 |
| 2003/0006371 A1 * | 1/2003 | Watanabe et al. | 250/310 |
| 2003/0058444 A1 * | 3/2003 | Nara et al. | 356/394 |
| 2004/0183013 A1 * | 9/2004 | Nakasuji et al. | 250/310 |
| 2006/0016992 A1 * | 1/2006 | Sato et al. | 250/311 |
| 2006/0060781 A1 * | 3/2006 | Watanabe et al. | 250/310 |
| 2006/0171593 A1 * | 8/2006 | Hayakawa et al. | 382/209 |
| 2007/0018101 A1 * | 1/2007 | Nakasuji et al. | 250/310 |
| 2007/0045536 A1 * | 3/2007 | Nakasuji et al. | 250/310 |
| 2007/0047800 A1 * | 3/2007 | Hiroi et al. | 382/149 |
| 2007/0114397 A1 * | 5/2007 | Hayakawa et al. | 250/307 |
| 2007/0210252 A1 * | 9/2007 | Miyamoto et al. | 250/310 |
| 2009/0001267 A1 * | 1/2009 | Enyama et al. | 250/310 |
| 2009/0039262 A1 * | 2/2009 | Nakasuji et al. | 250/310 |
| 2009/0208091 A1 * | 8/2009 | Hayakawa et al. | 382/149 |

FOREIGN PATENT DOCUMENTS

| | | |
|---|---|---|
| JP | 59-160948 | 9/1984 |
| JP | 2-15546 | 1/1990 |
| JP | 5-258703 | 10/1993 |
| JP | 6-338280 | 12/1994 |
| JP | 2002-26093 | 1/2002 |

OTHER PUBLICATIONS

Sandland, et al., "An electron-beam inspection system for x-ray mask production," J. Vac. Sci. Technol. B, Nov./Dec. 1991, pp. 3005-3009, vol. 9, No. 6, American Vacuum Society.

Meisburger, et al., "Low-voltage electron-optical system for the high-speed inspection of integrated circuits," J. Vac. Sci. Technol. B, Nov./Dec. 1992, pp. 2804-2808, vol. 10, No. 6, American Vacuum Society.

Meisburger, et al., "Requirements and performance of an electron-beam column designed for x-ray mask inspection," J. Vac. Sci. Technol. B, Nov./Dec. 1991, pp. 3010-3014, vol. 9, No. 6, American Vacuum Society.

"Electron/Ion Beam Handbook," pp. 622-623, The Nikkan Kogyo Shimbun. Ltd., Sep. 25, 1986 (first impression of the second edition issued); w/ partial English translation thereof.

* cited by examiner

Inspection detailed flow

Via chain structure (plan view)

Via chain structure (at the time of non-conduction)

Defect point inspection

FIG. 12-1

Inspection stripe position determination method

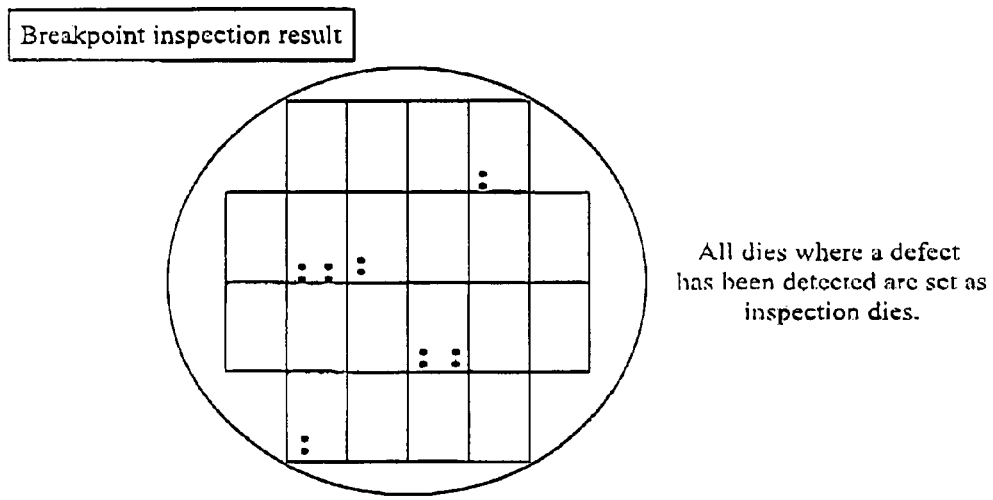

All dies where a defect has been detected are set as inspection dies.

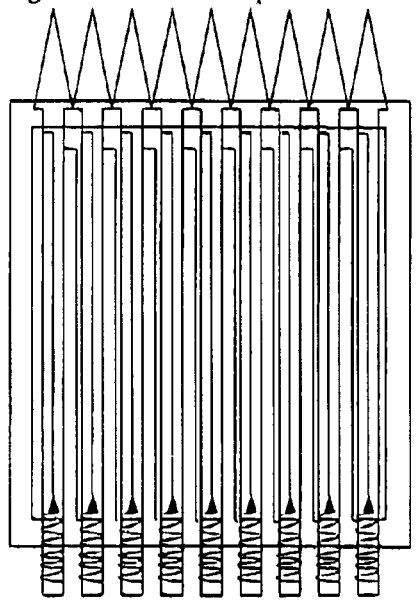

System 1 : Whole inspection region system
Whole inspection region in a die is inspected regardless of a defect position.

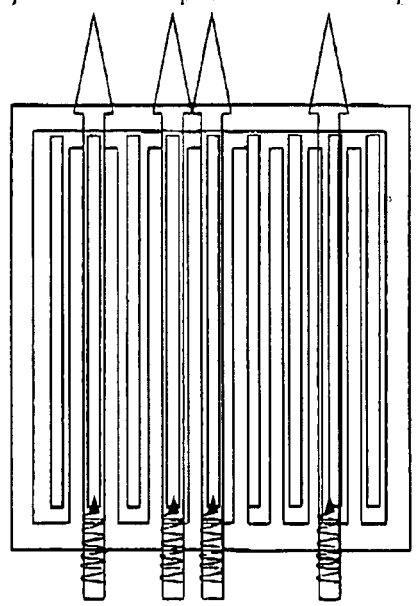

System 2 : All defect position system
Inspection stripes are determined so as to inspect all defect positions of the inspection die.

System 4 : Stripe unit system

System 5 : Mixed system

FIG. 13-1

Inspection stripe scanning order system

System 1: Normal sort system

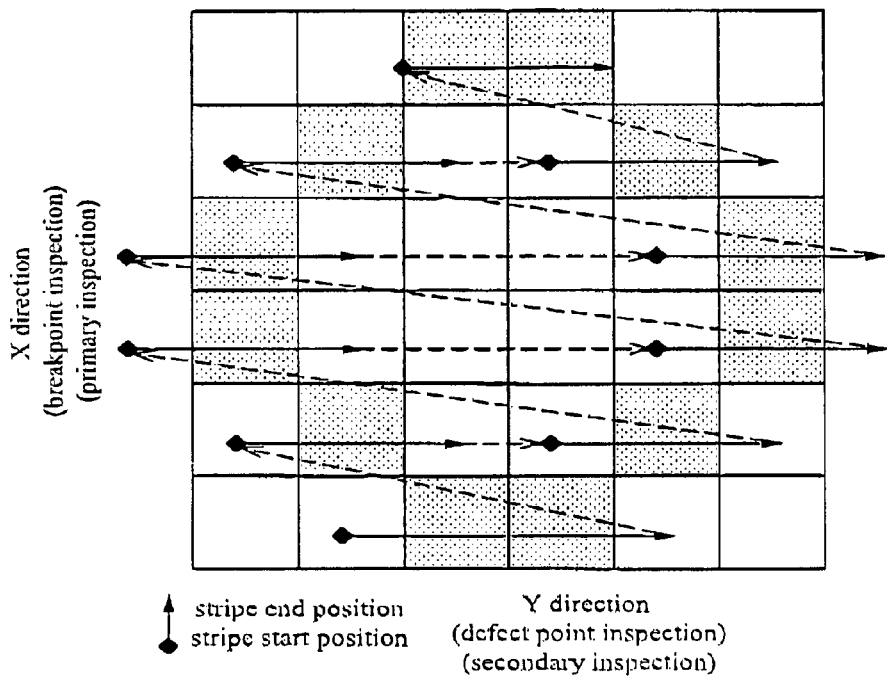

- Sorting is performed in a stripe order similar to that in nomal inspection.
X direction inspection
  Inspection is performed from the stripe whose die Y number is closest to 0.
  When die Y numbers are equal, the stripe whose die X number is closer to 0 has priority.
Y direction inspection
  Inspection is performed from the stripe whose die X number is closest to 0.
  When die X numbers are equal, the stripe whose die Y number is closer to 0 has priority.

FIG. 13-2

System 2 : Close sort system

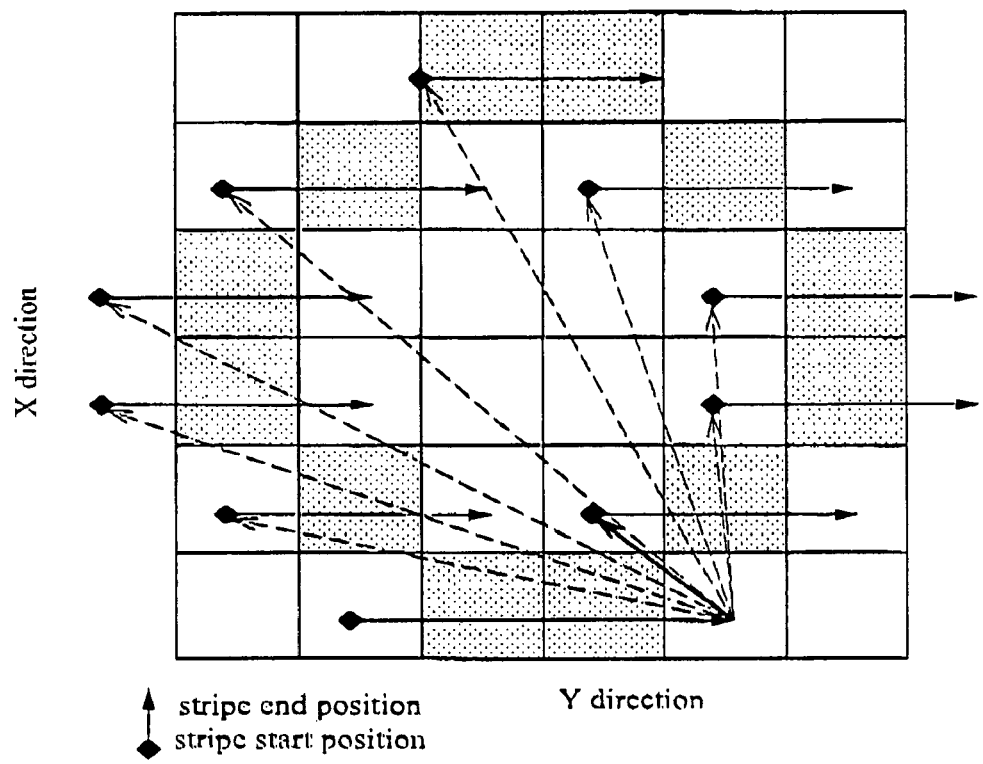

▲ stripe end position
◆ stripe start position

Y direction

- A stripe to be inspected next to a thick-line stripe is determined based on a movement distance to a start position of another stripe.
- In a case of the above diagram, since a movement distance of a thick broken line is shortest, a stripe directed by the thick broken line is inspected next to the thick line stripe.

System 3: Addition sort system

↕ stripe end position
◆ stripe start position

In a case of sorting the above stripes, when the first two stripes are registered by default, a movement distance between the stripes is as shown below by broken lines.

Y direction

FIG. 13-4

When (3) is added between (1) and (2), a movement distance between stripes is changed as shown below.

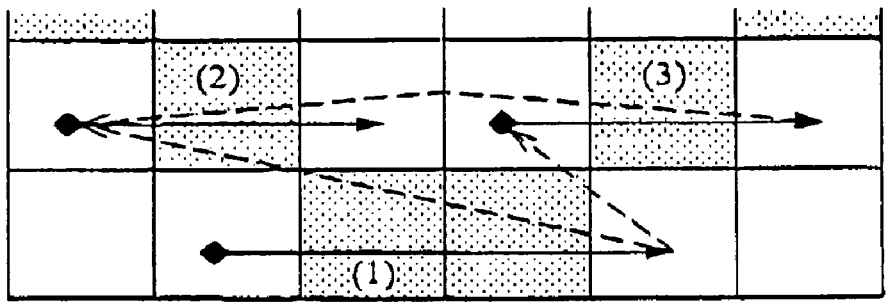

When (3) is added between (2) and (1), a movement distance between stripes is changed as shown below.

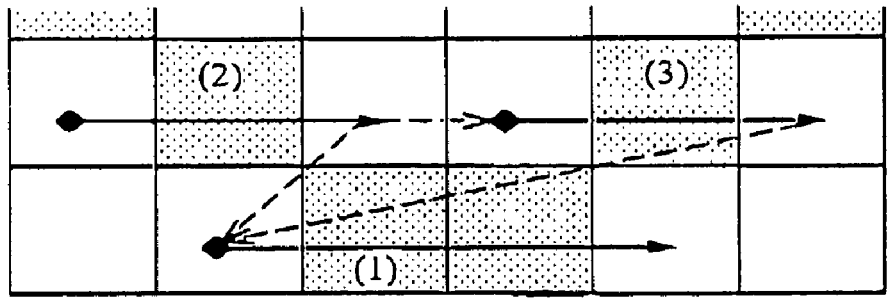

Since a distance of a broken line extended when (3) is added between (1) and (2) is shorter than a distance of a broken line extended when (3) is added between (2) and (1), adding (3) between (1) and (2) is employed.

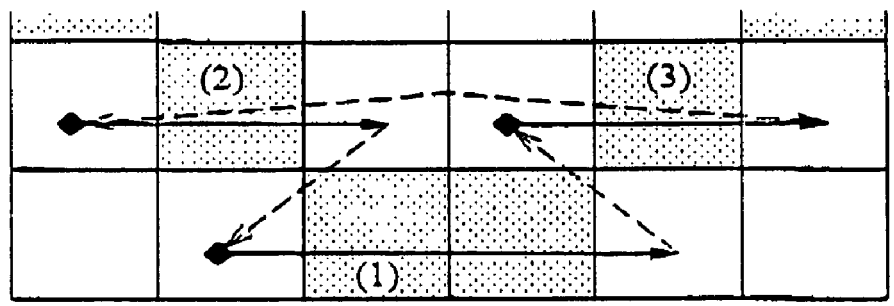

Y direction

FIG. 14-1

| Pixel size | 0.035 ▼ | μm |
| Inspection width | 31.4 ▼ | μm |

AUTO
31.4
49.3
67.2

FIG. 14-2

Time restriction (min) | 20 ▼ | ∨ interruption no time restriction
5
10
15
20
25
30

CIRCUIT PATTERN INSPECTION APPARATUS

CROSS-REFERENCE TO RELATED APPLICATION

The present application claims priority from Japanese Patent Application No. JP 2005-327541 filed on Nov. 11, 2005, the content of which is hereby incorporated by reference into this application.

TECHNICAL FIELD OF THE INVENTION

The present invention relates to a pattern inspection technology for a substrate having a fine circuit pattern of a semiconductor device, a liquid crystal display and others. More particularly, it relates to a pattern inspection technology for a pattern on a wafer during manufacturing process of a semiconductor device.

BACKGROUND OF THE INVENTION

An example of the inspection of a semiconductor wafer will be described. A semiconductor device is manufactured by repeating a step of transferring a pattern formed on a photomask onto a semiconductor wafer through lithography process and etching process. In a manufacturing process of a semiconductor device, the yield of the semiconductor device is largely influenced by quality of the lithography process, the etching process and others, generation of a foreign material, and the like. Therefore, in order to detect the generation of failures and defects in an early stage or in advance, a method for inspecting a pattern on a semiconductor wafer during the manufacturing process has been conventionally implemented.

As a method of inspecting a defect present in a pattern on a semiconductor wafer, a defect inspection apparatus that irradiates the semiconductor wafer with white light to compare equal circuit patterns of a plurality of LSIs by using an optical image has been put into practical use. Brief summary of the inspection system is described in "Monthly Semiconductor World" August, 1995, pp. 96-99 (Non-Patent Literature 1). Also, as inspection methods using an optical image, Japanese Patent Application Laid-Open Publication No. 3-167456 (Patent Literature 1) discloses a, system in which an image of an optically illuminated region on a substrate is formed by using a time-delay integrating sensor and the image and a design characteristic inputted in advance are compared to detect a defect, and Japanese Examined Patent Application Publication No. 6-58220 (Patent Literature 2) discloses a method in which image degradation at the time of image acquisition is monitored and the image degradation is corrected at the time of image detection, thereby performing a comparison inspection using a more stable optical image. When a semiconductor wafer is inspected in a manufacturing process by using such an optical inspection system, a residue and a defect of a pattern having a silicon oxide film or photosensitive photoresist material which is transmissive on its surface cannot be detected. In addition, etching residue and opening defect of a fine conduction hole which is smaller than a resolution power of an optical system cannot be detected. Further, a defect formed at a bottom portion of a step of a wiring pattern cannot be detected.

As described above, due to the miniaturization of circuit patterns, complexity of a circuit pattern shape and diversity of materials, defect detection by an optical image has become difficult. Therefore, a method of using an electron-beam image which is higher in resolution power than an optical image to perform a comparison inspection of a circuit pattern has been proposed, When the comparison inspection of a circuit pattern is performed by using an electron-beam image, it is necessary to acquire the image much faster than the observation performed by scanning electron microscopy (hereinafter, abbreviated as SEM) so as to achieve a practical inspection time. Further, it is also necessary to secure the resolution power of the image acquired at a high speed and an SN ratio of the image. As a comparison-inspection apparatus for a pattern by using an electron beam, J.Vac. Sci. Tech.B, Vol. 9, No. 6, pp. 3005-3009 (1991) (Non-Patent Literature 2), J.Vac. Sci. Tech. B, Vol. 10, No. 6, pp. 2804-2808 (1992) (Non-Patent Literature 3), Japanese Patent Application Laid-Open Publication No. 5-258703 (Patent Literature 3), and a patent specification of U.S. Pat. No. 5,502,306 (Patent Literature 4) disclose a method in which an electron beam having electron-beam current equal to or more than one hundred times the ordinary SEM (10 nA or more) is irradiated to a conductive substrate (x-ray mask or the like), any of generated secondary electrons, reflection electrons and transmission electrons are detected, and comparison inspection of an image formed from signals corresponding to the detected electrons is preformed, thereby automatically detecting a defect.

As a method of inspecting or observing a circuit board having an insulator by an electron beam, Japanese Patent Application Laid-Open Publication No. 59-155941 (Patent Literature 5) and "ELECTRON, ION BEAM HANDBOOK" (THE NIKKAN KOGYO SHIMBUN. LTD.) pp. 622-623 (Non-Patent Literature 4) disclose a method in which a stable image is acquired by low-accelerative electron-beam irradiation equal to or less than 2 keV so as to reduce influence of charge.

Further, Japanese Patent Application Laid-Open Publication No. 2-15546 (Patent Literature 6) discloses a method of irradiating ion from the rear side of a semiconductor substrate, and Japanese Patent Application Laid-Open Publication No. 6-338280 (Patent Literature 7) discloses a method of irradiating light to a surface of a semiconductor substrate to cancel the charge to an insulator, respectively. Furthermore, it becomes difficult to acquire a high-resolution image due to space charge effect in a case of a large-current and low-accelerative electron beam. Therefore, as a method of solving this problem, Japanese Patent Application Laid-Open Publication No. 5-258703 (Patent Literature 3) discloses a method of decelerating a high-accelerative electron beam just before a sample and irradiating a substantially low-accelerative electron beam to the sample.

As a method of acquiring an electron-beam image at high speed, Japanese Patent Application Laid-open Publication No. 59-160948 (Patent Literature 8) and Japanese Patent Application Laid-Open Publication No. 5-258703 (Patent Literature 3) disclose a method of successively irradiating an electron beam to a semiconductor wafer on a sample table while continuously moving the sample table, thereby acquiring the electron-beam image. Also, as a detection apparatus of a secondary electron used in a conventional SEM, a structure including a scintillator (Al-evaporated phosphor), a light guide and a photoelectron multiplier tube is adopted. Since the detection apparatus of this type detects emission from a phosphor, frequency responsiveness is poor, and it is unsuitable for forming an electron-beam image at high speed. In order to solve this problem, as a detection apparatus for detecting a high-frequency secondary electron signal, detecting means using a semiconductor detector is disclosed in Japanese Patent Application Laid-open Publication No. 5-258703 (Patent Literature 3).

SUMMARY OF THE INVENTION

In the conventional inspection, it is necessary to irradiate a charged particle beam to the whole surface of a region to be inspected of a semiconductor wafer to perform the inspection. Therefore, a lot of inspection time is required, which results in a quite inefficient work.

In addition, since inspection time is required for each semiconductor wafer, an inspection rate for detecting failures in a manufacturing line is lowered, and a semiconductor wafer where failures are generated cannot be extracted as a wafer to be inspected. Therefore, due to the inspection based upon the low statistical random extraction, an outflow of a defective product cannot be prevented.

On the other hand, in order to perform inspection with high detection accuracy while shortening an inspection time, Japanese Patent Application Laid-Open Publication No. 2002-26093 (Patent Literature 9) discloses a method of performing the inspection in which the number of scanning lines to a whole region to be inspected is thinned by 1/n.

However, according to the result of examination performed by the inventors of the present invention, it has become apparent that, although a certain effect to a random defect can be achieved, the method includes various defects, that is: it is difficult to uniquely determine the number of scanning lines to be thinned in the inspection for maintaining a high detection accuracy; and when a critical defect remains in a region where thinning has been performed for a system defect, inspection becomes utterly meaningless even if the number of semiconductor wafers to be inspected is increased.

As apparent from the above, none of the conventional examples has provided a technology for accurately and efficiently detecting major defects in a short time such as interwire short-circuit due to a barrier metal residue, non-conduction due to insufficient etching or etching gas reaction product in a contact plug/via plug forming process, and via chain conduction failure due to opening defect caused by plug-opening blocking material which is a foreign material generated in the etching process, and none of them realizes an optimal inspection of an electric defect.

An object of the present invention is to provide a technology for detecting a defect on a main surface of a semiconductor wafer at high speed by taking advantage of characteristics of a potential contrast method using a defect inspection structure and an electron bean defect detection apparatus which are presented in this specification or an inspection and analysis apparatus based upon them, thereby improving the capture efficiency of a critical electric defect and the search efficiency of a defective portion.

The present invention is a circuit pattern inspection apparatus comprising: irradiation means for irradiating an irradiation beam including light, a laser beam, or a charged particle beam to a surface of a substrate of a wafer having a circuit pattern formed thereon; a stage on which the wafer is mounted for moving the wafer in an arbitrary direction; stage control means for controlling the movement of the stage; detection means for detecting a signal generated from the substrate by the irradiation; storage means for imaging the signal detected by the detection means to store the same; comparison means for comparing the stored image with an image formed from another equal circuit pattern; and determination means for determining a defect on the circuit pattern from the comparison result, wherein a determination function to determine the defect in a stripe through a primary inspection where an irradiation beam is irradiated to perform scanning of the irradiation beam and a secondary inspection where an irradiation beam is irradiated to perform scanning of the irradiation beam in a longitudinal direction of the stripe of an inspection region where a defect determined by the primary inspection is present is provided.

According to the present invention, since the stripe of the inspection region where the defect is present is determined in the primary inspection and a position of the defect on the stripe can be detected in the secondary inspection, inspection is rapidly performed compared with a conventional one which performs the irradiation and scanning to the whole surface of the wafer.

Further, the primary inspection and the secondary inspection are performed by changing only the direction of irradiation and scanning. Since it is unnecessary to rotate the direction of a wafer, the primary inspection and the secondary inspection can be preformed continuously, and therefore, rapid inspection can be achieved. Accordingly, a throughput of a circuit pattern inspection method can be enhanced.

BRIEF DESCRIPTIONS OF THE DRAWINGS

FIG. 12-1 is a diagram showing an inspection stripe position determination method according to the embodiment of the present invention (systems 1 and 2);

FIG. 12-2 is a diagram showing the inspection stripe position determination method according to the embodiment of the present invention (system 3);

FIG. 12-3 is a diagram showing the inspection stripe position determination method according to the embodiment of the present invention (systems 4 and 5);

FIG. 13-1 is a diagram showing an inspection stripe scanning order determination system according to the embodiment of the present invention (system 1);

FIG. 13-2 is a diagram showing the inspection stripe scanning order determination system according to the embodiment of the present invention (system 2);

FIG. 13-3 is a diagram showing the inspection stripe scanning order determination system according to the embodiment of the present invention (system 3);

FIG. 13-4 is a diagram showing the inspection stripe scanning order determination system according to the embodiment of the present invention (explanation about addition of system 3);

FIG. 14-1 is a diagram showing a deflection width reducing method for an inspection stripe according to the embodiment of the present invention; and FIG. 14-2 is a diagram showing a method for defining an inspection time of the inspection stripe according to the embodiment of the present invention.

DESCRIPTIONS OF THE PREFERRED EMBODIMENTS

An example of an inspection method and an inspection apparatus of an embodiment of the present invention will be described below in detail with reference to the drawings.

Figure 1:
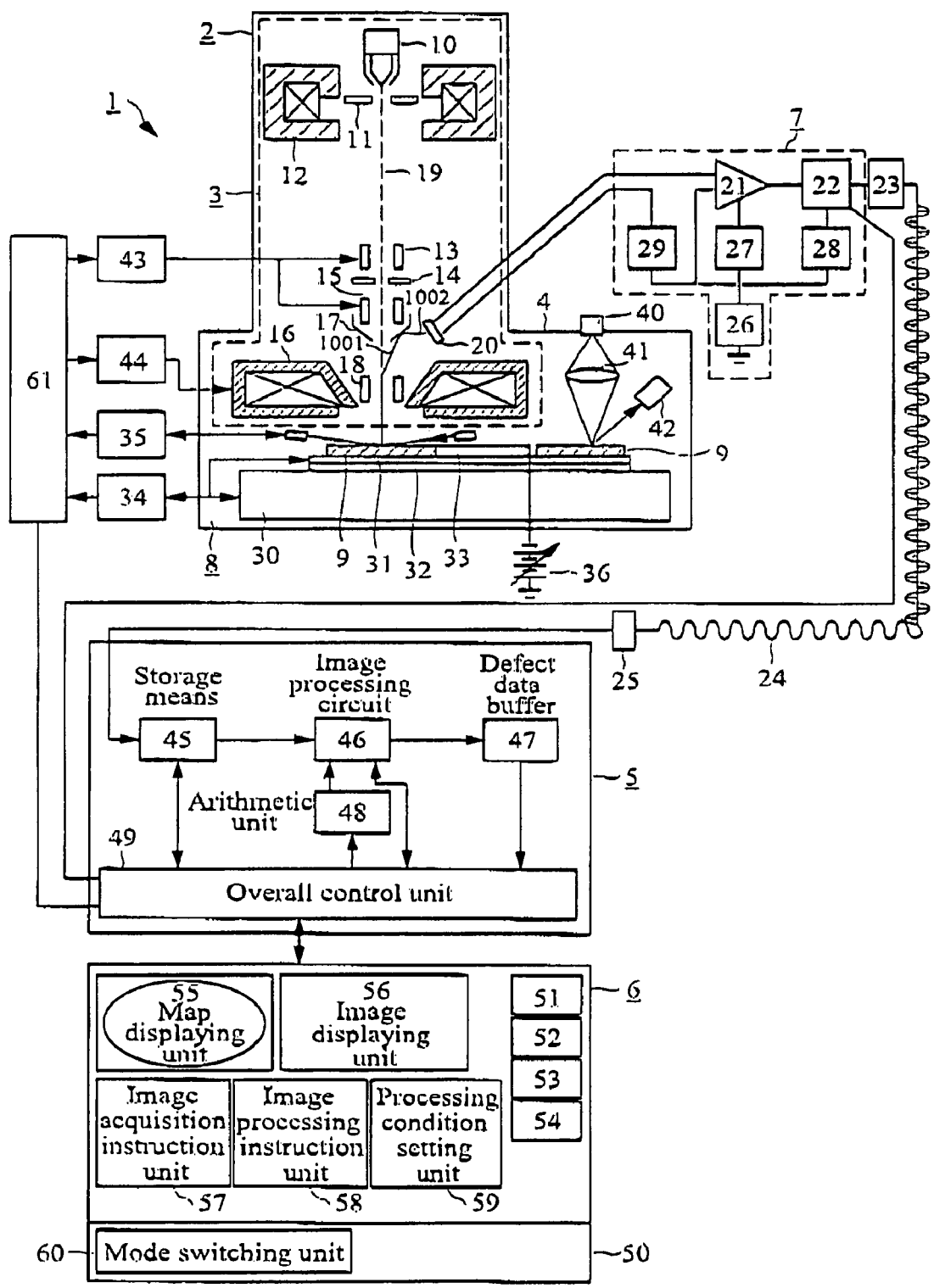
FIG. 1 is a configuration diagram showing a circuit pattern inspection apparatus using charged particles according to an embodiment of the present invention.

FIG. 1 is a diagram showing a configuration example of a circuit pattern inspection apparatus 1 of the present invention using a charged particle beam. The circuit pattern inspection apparatus 1 is provided with an evacuated inspection chamber 2 and a preparation chamber (not shown in this embodiment) for conveying a substrate to be inspected 9 into the inspection chamber 2.

The preparation chamber is constituted so as to be evacuated independently of the inspection chamber 2. Further, the circuit pattern inspection apparatus 1 is composed of a control unit 5 and an image operating unit 6 in addition to the inspection chamber 2 and the preparation chamber described above.

The inspection chamber 2 is roughly composed of an electron optical system 3 which is lighting means, a secondary electron detection unit 7 which is detection means, a sample chamber 8, and an optical microscope unit 4. The electron optical system 3 is composed of an electron gun 10 which emits an electron beam which is an irradiation beam, an electron-beam leading electrode 11, a condenser lens 12, a blanking deflector 13, a scanning deflector 15, a diaphragm 14, an objective lens 16, a reflecting plate 17 and an EXB deflector 18.

A secondary electron detector 20 of the secondary electron detection unit 7 is disposed above the objective lens 16 in the inspection chamber 2. An output signal of the secondary electron detector 20 is amplified by a preamplifier 21 provided outside the inspection chamber 2 and then converted into digital data by an AD converter 22.

The sample chamber a is composed of a sample table 30, an X stage 31, a Y stage 32, and a rotating stage 33, a position monitoring meter 34 and an inspected substrate height meter 35. The movement of the stage is controlled by stage control means.

The optical microscope unit 4 is provided at a position near the electron optical system 3 in the inspection chanter 2 but separated from the system 3 to some extent so as to prevent the mutual interference between the optical microscope unit 4 and the electron optical system 3, and a distance between the electron optical system 3 and the optical microscope unit 4 is well-known.

The X stage 31 or the Y stage 32 reciprocates the known distance between the electron optical system 3 and the optical microscope unit 4. The optical microscope unit 4 is composed of a white light source 40, an optical lens 41 and a CCD camera 42.

The control unit 5 is composed of a storage unit 45, an image processing circuit 46, a defect data buffer 47, and an arithmetic unit 48. An electron-beam image or optical image which has been taken in is displayed on a monitor 50. An operation instruction and an operation condition of each unit of the apparatus are inputted from the control unit 5.

Also, the control unit 5 has an overall control unit 49. A correction control 61 is controlled by the overall control flit 49.

The image operating unit 6 has a map displaying unit 55, an image displaying unit 56, an image acquisition instructing unit 57, an image processing instructing unit 58, a processing condition setting unit 59, an inspection unit 51, a printing unit 52, a file saving unit 53, an image saving unit 54, and mode switching means 60.

In the control unit 5, conditions such as an accelerating voltage at the generation of an electron beam, a deflection width and a deflection speed of an electron beam, a signal loading timing of a secondary electron detection unit, and a sample table movement speed are inputted in advance so that they can be set arbitrarily or selectively for any purpose.

An irradiation beam which is an electron beam swings right and left with respect to its irradiation and scanning direction. A deflection region width due to the swinging can be changed arbitrarily by the control unit 5.

The irradiation beam swings in a primary inspection and/or a secondary inspection described later, and the deflection region width which is an amplitude width can also be changed in the primary inspection and/or the secondary inspection.

The control unit 5 uses a correction control circuit 43 to monitor deviation of a position or a height based on signals from the position monitoring meter 34 and the inspected substrate height meter 35, generates a correction signal from the monitoring result, and transmits the correction signal to an objective lens power source 44 and the scanning deflector 15 so as to constantly irradiate an electron beam to a correct position.

When acquiring an image of the substrate to be inspected 9, a narrowed primary electron beam 19 is irradiated to the substrate to be inspected 9 to generate secondary electrons 1001, and they are detected in synchronization with the scanning of the primary electron beam 19 and the movement of the stages 31 and 32, thereby acquiring an image on the surface of the substrate to be inspected 9. It is essential that an inspection rate is high in an automatic inspection apparatus.

Therefore, scanning of an electron beam of an electron-beam current in pA order at low speed, multiple scannings and superposition of respective images are not performed unlike the conventional SEM. Also, in order to suppress the charge to an insulating material, an electron-beam scanning must be performed once or at most several times at high speed.

Therefore, in this embodiment, an image is formed by performing scanning only once by a large current electron beam of 100 nA which is about one hundred times the electron beam of the ordinary SEM or more. Note that it is assumed here that the scanning width is 100 μm, one pixel is a square with one side of 0.1 μm, and one scanning is performed in 1 μs.

A thermal field emission electron source of a diffusion supplementation type is used for the electron gun 10. By using the electron gun 10, a stable electron-beam current can be secured compared with, for example, a conventional tungsten (W) filament electron source and a conventional electron source of cool field emission type. Therefore, an electron-beam image whose luminance fluctuation is reduced can be obtained.

Further, since the electron gun 10 makes it possible to set a large electron-beam current, a high-speed inspection as described later can be realized. The primary electron beam 19 is led from the electron gun 10 by applying a voltage between the electron gun 10 and the leading electrode 11.

The primary electron beam 19 is accelerated by applying a high-voltage negative potential to the electron gun 10. By this means, the primary electron beam 19 travels toward the sample table 30 with the energy corresponding to the potential, and it is converged by the condenser lens 12 and further narrowed by the objective lens 16, and then irradiated to the substrate to be inspected 9 (a semiconductor wafer, a chip, or a substrate having a fine circuit patterns such as a liquid crystal and a mask) placed on the X and Y stages 31 and 32 on the sample table 30.

Further, a scanning signal generator 43 for generating a scanning signal and a blanking signal is connected to the blanking deflector 13, and a lens power source 44 is connected to the condenser lens 12 and the objective lens 16.

A negative voltage can be applied to the substrate to be inspected 9 from a retarding power source 36. By adjusting a voltage of the retarding power source 36, the primary electron beam is decelerated, and an electron-beam irradiation energy to the substrate to be inspected 9 can be adjusted to an optimal value without changing the potential of the electron gun 10.

The secondary electrons 1001 generated by irradiating the primary electron beam 19 to the substrate to be inspected 9 are accelerated by a negative voltage applied to the substrate to be inspected 9. The ExB deflector 18 is disposed above the substrate to be inspected 9, and the accelerated secondary electrons 1001 are deflected in a predetermined direction by the ExB deflector 18.

A deflection amount can be adjusted according to the magnitude of a voltage applied to the ExB deflector 18 and the intensity of a magnetic field. Also, the magnetic field can be changed in conjunction with a negative voltage applied to the sample The secondary electrons 1001 deflected by the ExB deflector 18 collide against the reflecting plate 17 under a predetermined condition.

The reflecting plate 17 is united with a shield pipe of a deflector of an electron beam to be irradiated to the sample (hereinafter, called "primary electron beam") and is formed in a cone shape. When the accelerated secondary electrons 1001 collide against the reflecting plate 17, second secondary electrons 1002 having energy of several V to 50 ev are generated from the reflecting plate 17.

The secondary electron detection unit 7 is composed of a secondary electron detector 20 located inside the evacuated inspection chamber 2, and a preamplifier 21, an AD converter 22, optical conversion means 23, optical transmission means 24t, electrical conversion means 25, a high-voltage power source 26, a preamplifier driving power source 27, an AD converter driving power source 28 and a reverse bias power source 29 located outside the inspection chamber 2.

As described above, the secondary electron detector 20 in the secondary electron detection unit 7 is disposed above the objective lens 16 in the inspection chamber 2. The secondary electron detector 20, the preamplifier 21, the AD converter 22, the optical conversion means 23, the preamplifier driving power supply 27, and the AD converter driving power supply 28 are floating at a positive potential due to the high-voltage power source 26.

The second secondary electrons 1002 generated due to collision on the reflecting plate 17 are directed to the secondary electron detector 20 due to an attracting field of the second secondary electrons 1002. The secondary electron detector 20 is configured so as to detect the second secondary electrons 1002 generated by the collision of the secondary electrons 1001, which are generated during the time when the primary electron beam 19 is irradiated to the substrate to be inspected 9 and then accelerated, to the reflecting plate 17 in conjunction with scanning timing of the primary electron beam 19.

An output signal of the secondary electron detector 20 is amplified by the preamplifier 21 provided outside the inspection chamber 2 and is converted into digital data by the AD converter 22. The AD converter 22 is configured so as to convert an analog signal detected by the secondary electron detector 20 into a digital signal just after it is amplified by the preamplifier 21 and then transmit the same to the image processing unit 5.

Since the detected analog signal is digitized just after the detection and then transmitted, a signal having a high SN ratio can be obtained at higher speed than ever before.

The substrate to be inspected 9 is placed on the X and Y stages 31 and 32, and it is possible to select either one of a method where the X and Y stages 31 and 32 are not moved to scan the primary electron beam 19 two-dimensionally at the time of inspection and a method where the X and Y stages 31 and 32 are continuously moved in a Y direction at a fixed speed to scan the primary electron beam 19 linearly in an X direction at the time of inspection.

When a relatively small specific region is to be inspected, the former method where the stages are not moved to perform the inspection is effective, and when a relatively-wide region is to be inspected, a method where the stages are continuously moved at a fixed speed to perform the inspection is effective.

When the primary electron beam 19 is required to be blanked, the primary electron beam 19 is deflected by the blanking deflector 13, and the electron beam is controlled so as not to pass through the diaphragm 14. As the position monitoring meter 34, a length meter utilizing a laser interference is used in this embodiment.

Positions of the X stage 31 and the Y stage 32 can be monitored in real time and transferred to the control unit 5. Also, data such as the numbers of rotations of motors for the X stage 31, the Y stage 32, and the rotating stage 33 is transferred from respective drivers to the control unit 5.

The control unit 5 is designed to correctly acquire a region and a position to which the primary electron beam 19 is irradiated based on these data, and displacement of an irradiated position of the primary electron beam 19 is corrected by the correction control circuit 43 in real time according to need. Also, a region where an electron beam is irradiated can be stored for each substrate to be inspected.

As the inspected substrate height meter 35, an optical measuring device employing a measuring method other than that using an electron beam, for example, a laser interferometry measuring device and a reflected light measuring device which measures the changes based on a position of a reflected light are used, and the inspected substrate height meter 35 is configured so as to measure a height of the substrate to be inspected 9 placed on the X and Y stages 31 and 32 in real time.

In this embodiment, a system in which an elongated white light that has passed through the slit is irradiated to the substrate to be inspected 9 through a transparent window, and a position of a reflected light is detected by a position detecting monitor to calculate an amount of height change based on the position fluctuation is used.

Based on the measurement data by the inspected substrate height meter 35, a focal length of the objective lens 16 for narrowing the primary electron beam 19 is dynamically corrected, and the primary electron beam 19 constantly focused on a region to be inspected can be emitted.

Since warpage and height distortion of the substrate to be inspected 9 is measured before electron beam irradiation, correction condition for each inspection region of the objective lens 16 can be set based on the measured data. The control unit 5 is composed of the storage unit 45 as storage means, the image processing circuit 46, the defect data buffer 47 and the arithmetic unit 48.

An image signal of the substrate to be inspected 9 detected by the secondary electron detector 20 is amplified by the preamplifier 21, converted into an optical signal by the optical conversion means 23 after being digitized by the AD converter 22, transmitted by the optical transmission means 24, and then stored in the storage means 45 after being converted into an electrical signal again by the electrical conversion means 25.

The image processing circuit 46 performs the positioning of images separated from each other by a certain distance, the standardization of a signal level, and various image processings for removing a noise signal based on the stored image signal and also performs a comparison operation of the image signals.

An absolute value of a differential image signal after the comparison operation is compared with a predetermined threshold (comparison means), and when a differential image signal level is larger than the predetermined threshold, the pixel is determined as an defect candidate (determination means), and the position thereof, the number of defects and others are displayed on the monitor 50.

Though described later, the image processing circuit 46 sad determination means provided in the control unit 5 have a function to perform the primary inspection where irradiation beam is irradiated to the inspection wafer 104 to scan the same and to determine a defect in a stripe of an inspection region where a defect determined in the primary inspection is present along a longitudinal direction of the stripe.

Figure 4:
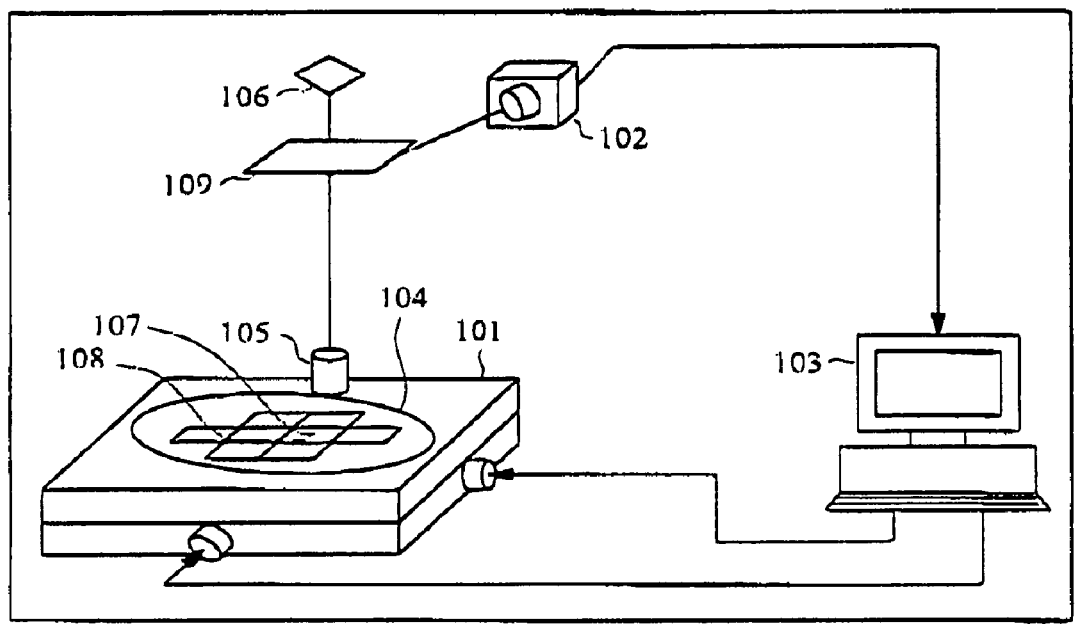
FIG. 4 is a configuration diagram of the circuit pattern inspection apparatus using light and/or a laser beam according to the embodiment of the present invention.

Next, a whole configuration of a wafer appearance inspection apparatus in the case of using light or a laser beam as a light source will be described. FIG. 4 is a block diagram showing the whole configuration of the wafer appearance inspection apparatus according to the embodiment of the present invention. The inspection wafer 104 is placed on an X-Y stage 101.

chips are formed and arranged regularly in a lattice pattern on the inspection wafer 104. A control unit 103 moves the X-Y stage 101 by a distance corresponding to several times the chip pitch. The light from a light source 106 is irradiated to the inspection wafer 104.

Light reflected by the inspection wafer 104 passes through an objective lens 105 and is subjected to light path division by a half mirror 109, and then detected as a two-dimensional image by a CCD camera 102.

The X-Y stage 101 is moved by a chip pitch by the control unit 103, and images at equal points on an inspection chip 107 and a comparison chip 108 can be acquired.

The control unit 103 determines that a defect is present on the inspected point of the inspection chip 107 when a difference in contrasting density between the equal points on the inspection chip 107 and the comparison chip 108 is larger than a predetermined threshold.

Figure 2:
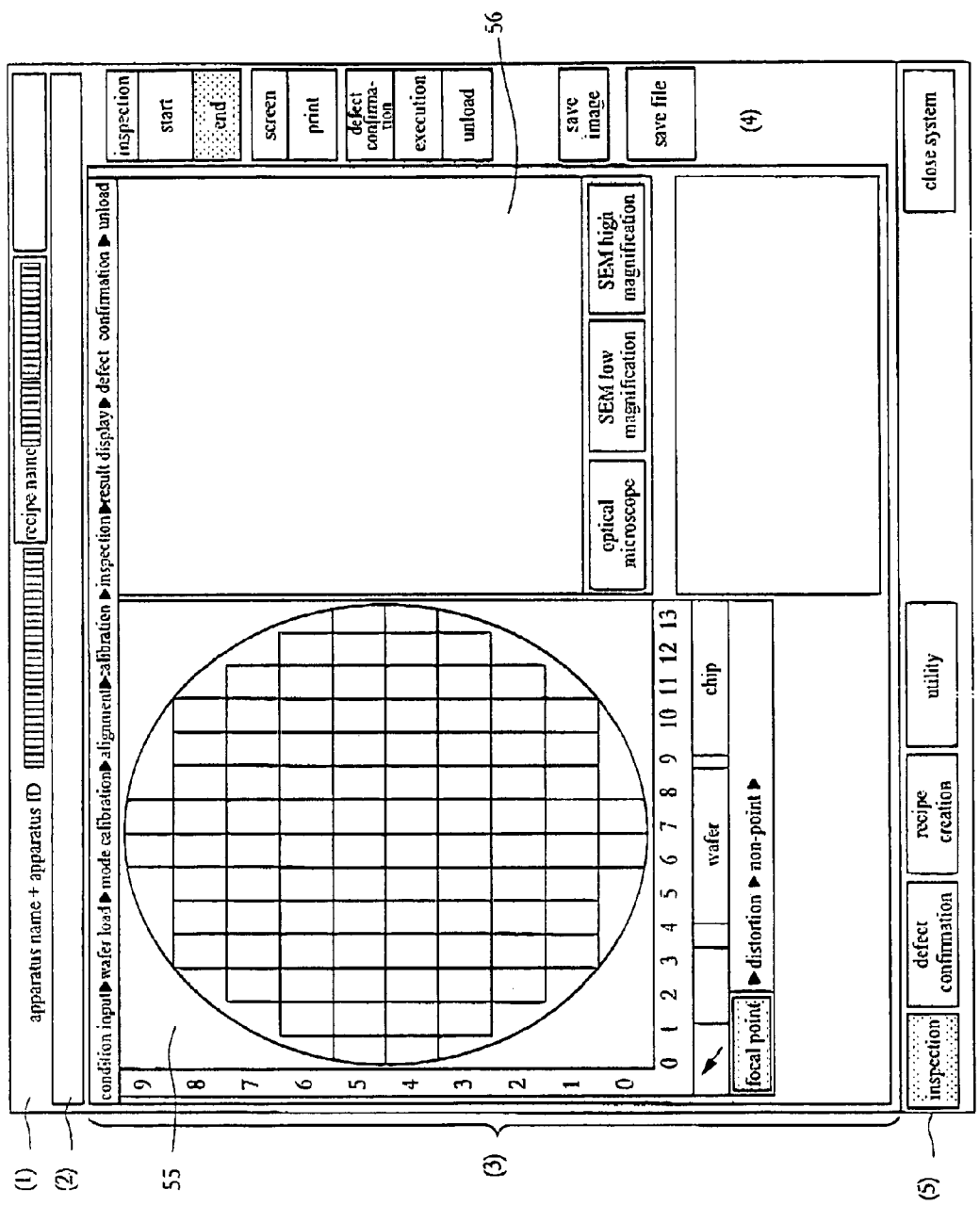
FIG. 2 is a configuration diagram showing a monitor unit of the circuit pattern inspection apparatus according to the embodiment of the present invention.

FIG. 2 is a diagram showing a configuration example of a monitor unit. A screen of the monitor is roughly divided into 5 regions. A region (1) is disposed at an upper portion of the screen, where an apparatus name, an apparatus ID, a type file name and a process file name as a recipe name, and others are displayed. A guidance which explains an operation or a state is displayed on a region (2). A map display portion 55 and an image display portion 56 are included in a region (3) positioned at a central portion of the screen, where a displayed content is changed according to an operation or progress thereof.

Operation buttons commonly required for a plurality of screens are displayed on a region (4) positioned on the right side of the screen, where there are "print", "save file", "start", "end", "save image" and others. For example, when "save file" is pressed, a screen where the names of kind file and the process file in which a currently created recipe is saved are designated is displayed.

Also, when "save image" is pressed, a screen where a name for saving a currently displayed image as an image file is designated is displayed. A mode name is displayed on ax operation region (5) in a lower portion of the screen. For example, when "inspection" is pressed, a mode for executing automatic inspection is started, and when "recipe creation" is pressed, a mode for inputting a parameter is started.

Figure 3:
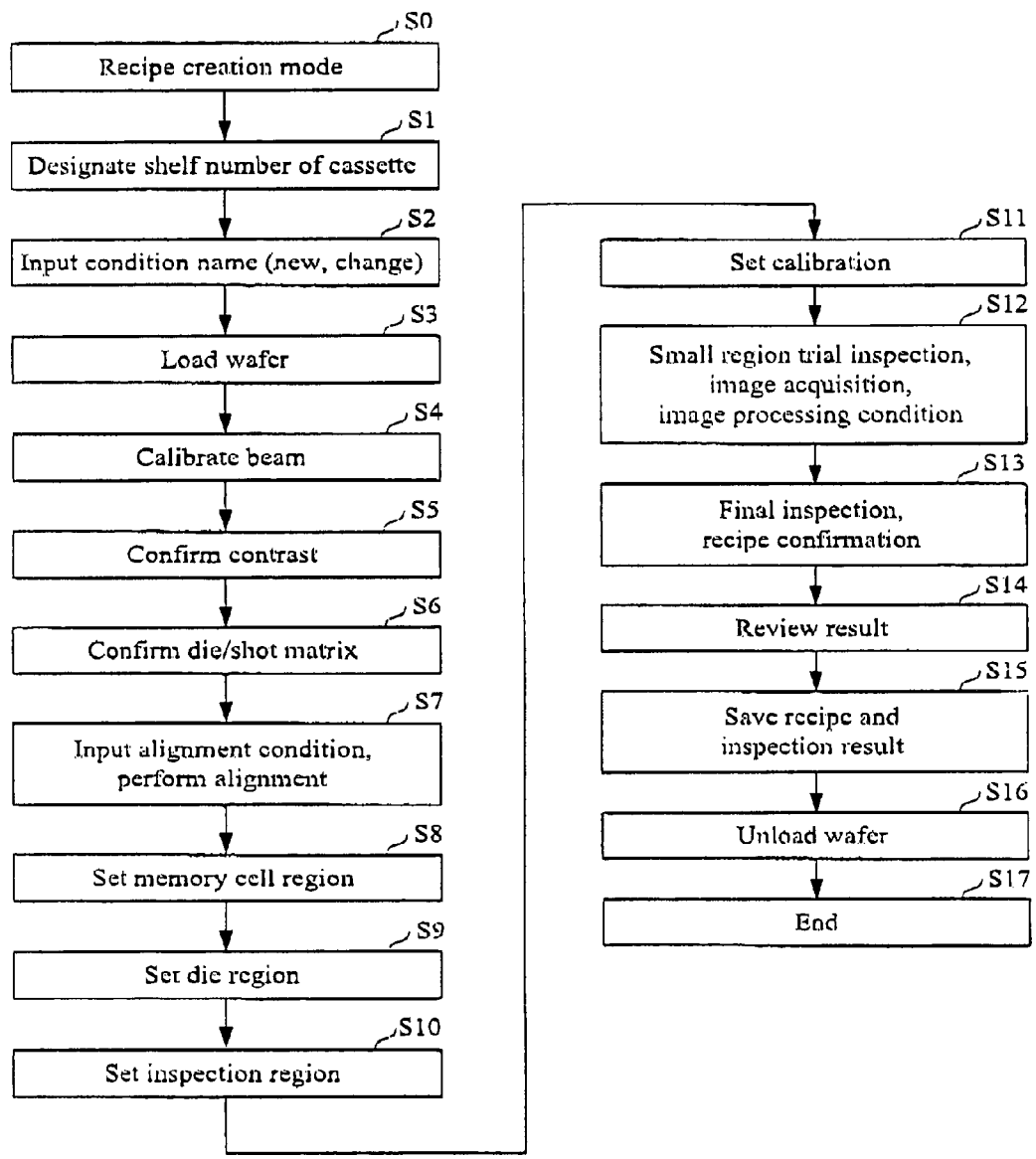
FIG. 3 is a flowchart showing a recipe creation processing of the circuit pattern inspection apparatus according to the embodiment of the present invention.

Next, a method for creating a recipe will be described. A processing flow of a recipe creation mode is shown in FIG. 3. When a "recipe creation" mode is selected on an initial screen in FIG. 2, mode switching means 60 functions to switch the initial screen to a screen (S0) for recipe creation shown in FIG. 3.

When a start button is pressed on this screen, the shelf number of a cassette is displayed, and a shelf number is first designated (S1). Next, a recipe file is called up to perform input of type condition about new or change and input of a lot ID and a wafer ID (S2). This change means a change of a recipe creation condition regardless of loading/unloading, and the change is mainly performed with loading.

Incidentally, since a recipe of another device described later cannot be inputted directly, a file of an inspection result (a defect information or data file: the content of this file is open to a user) is inputted, the inputted file is converted to produce a recipe for the device, and it is changed in this step in order to compensate for insufficient data.

The new creation will be described here. Then, a wafer cassette is provided in a loader of the inspection apparatus (S3). The processing items include: (1) detecting OF or a notch; (2) retaining it in a sample holder (sample changing chamber); and (3) transferring the sample holder to an inspection chamber stage.

Next, movement to a stage reference mark is performed to perform absolute calibration of a beam (S4). Here, calibration based on a default recipe file condition is performed, where (1) beam irradiation, (2) deflection correction, reference coordinate correction, and (3) focal point parameter correction are performed.

Next, an electron beam is irradiated to a specific position on the sample to readjust a focal point and a non-point after the confirmation of image contrast on the sample (S5). At this time, when enough contrast cannot be obtained, an electron beam irradiation conditions are changed. The irradiation conditions and conditions of the focal point and the non-point designated here are stored in the process file as a recipe parameter.

After the electron beam irradiation condition is determined and the contrast is confirmed, a shot of the wafer and the size and the arrangement of the dies (chips) are inputted (S6) After a shot size and a shot matrix are inputted and arrangement of the die in the shot is inputted, a shot around a wafer or presence or absence of the die is designated. The shot and the die arrangement which are set here are stored as parameters in a recipe file.

Next, alignment condition is inputted and alignment is executed (S7). More specifically, (1) designation of alignment chip (plural points), (2) movement to a first chip origin, (3) switching of an optical microscope monitor, and (4) manual movement to an alignment mark position of the first chip are performed.

Further, (5) registration of an optical image, (6) switching to a SEM image mode, (7) manual fine-adjustment to the alignment mark position, (8) registration of a SEM image, and (9) registration of alignment coordinates are performed. Also, as items of alignment execution, (1) movement to a first point, (2) image input/search/matching, (3) movement to a second point, (4) image input/search/matching, (5) movement to a remaining point, search, matching, and (6) correction of inclination/position/chip interval are performed.

In addition, as offset setting of a chip origin, (1) movement to a final point alignment mark, (2) alignment mark position designation (SEM image mode), (3) movement to the first chip origin, (4) chip origin position designation (SEM image mode), (5) offset calculation and registration of the chip origin-alignment mark are performed. The offset of the chip origin means a distance between the alignment coordinates and the origin coordinates of a chip where a mark of the alignment coordinates is present.

In this manner, the offset value between the designated alignment pattern coordinates and the chip origin is inputted and registered as the alignment parameter in the step file. In the recipe creation, since there are many parameters for designating coordinates for performing various processings on the wafer, an alignment condition is first defined and registered and steps up to the alignment are performed.

Next, a memory cell region setting in the chip is performed (S8). As items thereof, (1) cell region inputting, (2) cell pitch inputting, and (3) registration of the cell region (1) and the cell pitch (2) are performed. Inputting of the cell region is performed using an optical microscope image or an electron beam image.

Next, die region setting is performed (S9). As items thereof, (1) die region inputting, (2) die non-inspection region inputting, and (3) registration of the die region (1) and the die non-inspection region (2) are performed. Inputting of the die region is also performed using an optical microscope image or an electron beam image.

Next, an inspection region is designated (S10). In tile designation of the inspection region, two types of an inspection die and an inspection region in the die can be designated. When it is unnecessary to inspect all the dies or when it is desired to inspect only a specific region in a die, designation can be performed arbitrarily as described later.

Further, an inspection sampling rate to a designated region can be designated. Also, an inspecting direction can be designated. Data about the die region and the inspection region is stored as parameters in the step file.

When designation of the inspection region is completed, the process proceeds to calibration setting for adjusting luminance at the inspection (S11). In the calibration, an image is acquired and gain adjustment of hardware and luminance correction are performed according to a signal amount based upon a luminance distribution of the image.

In an actual case, the calibration is performed by designating a die to be calibrated and designating coordinates in the die. A coordinate value where the calibration is performed, a gain of the luminance, the offset value are stored as parameters in the step file.

Next, an image is actually acquired under the various conditions set above and an image processing condition for detecting a defect is set (S12). First, when the image is to be acquired, a type of a filter to be applied to a detection signal is selected.

Then, an image of a small region in one chip is acquired under the same condition as an actual inspection. Here, the small region means, for example, a region having a width of 100 μm corresponding to a scanning width of an electron beam and a length corresponding to one chip. After the image is acquired, a threshold for determining a defect is inputted and an image of a portion determined as a defect is displayed.

By repeating the steps described above, an optimal inspection condition is determined. This series of steps or works is called "small region trial inspection". The parameters of the threshold and the files which are set here are stored as parameters of an in-step file.

Various parameters required for inspection can be set through the various inputs described above. However, in an actual semiconductor wafer, since there are variations in wafer plane and processes between manufacture lots, image processing condition setting in the small region trial inspection is insufficient, and it is necessary to determine a threshold for defect determination with taking these variations into account.

Therefore, a final inspection is performed using the created recipe file (S13). More specifically, (1) a stage is continuously moved at constant speed and a position and a height of the stage are monitored, (2) beam scanning and real time correction (stage/Z-sensor tracking) are performed, (3) secondary electron detection, AD conversion, and image memory inputting are performed, (4) image processing and comparison determination are performed, (5) beam correction for each of N stripes is performed, and (6) the number of detects and defect position are displayed.

Figure 5:
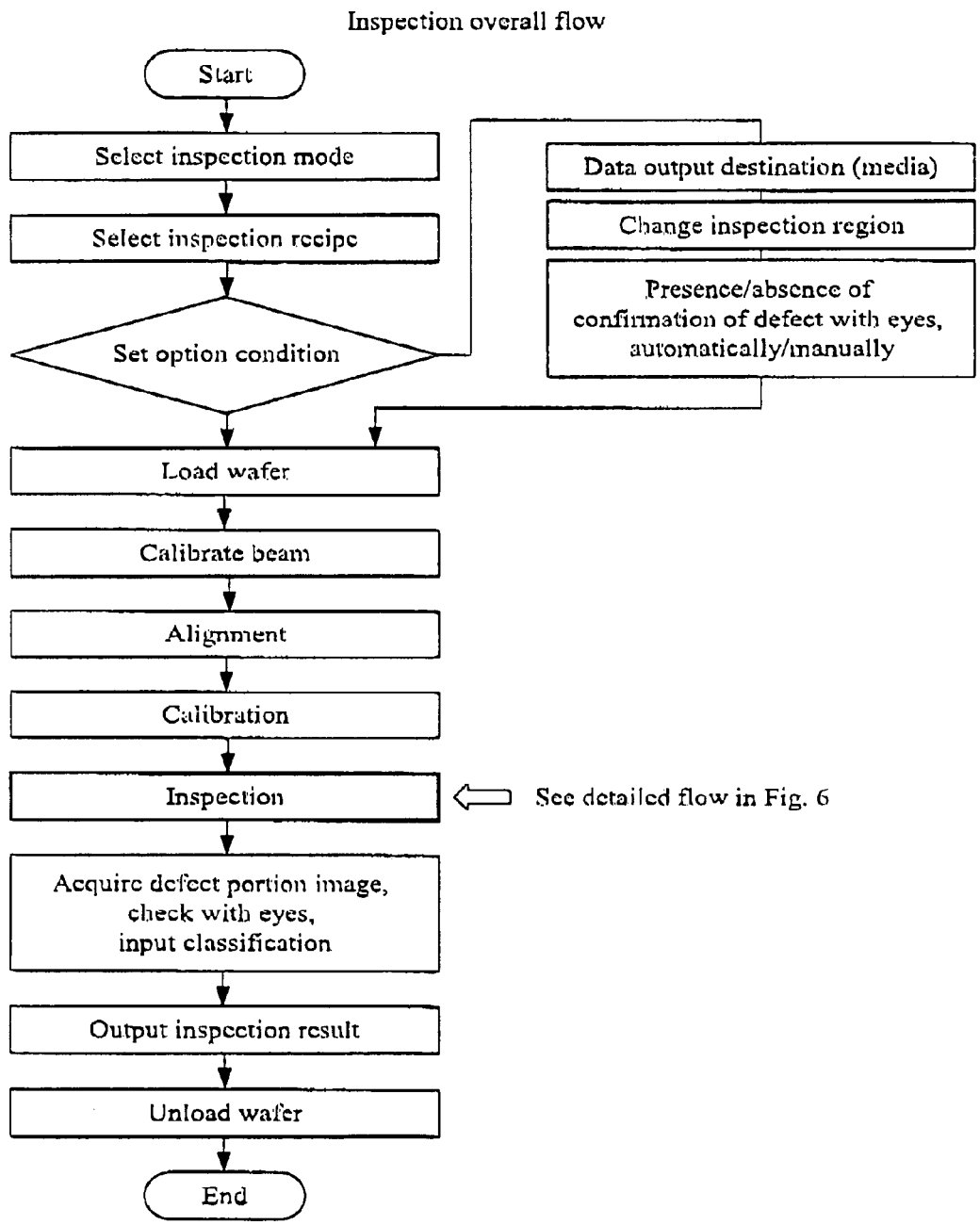
FIG. 5 is an explanatory diagram showing an overall flow of the inspection according to the embodiment of the present invention.

According to the monitoring result, a defect detection level and an error detection level are confirmed (S14), and when the confirmed levels finally satisfy appropriate conditions, the various parameters inputted before are registered in the type file and the step file (S15). Finally, the wafer is unloaded (S16).

a overall inspection flow will be described with reference to FIG. 5. An inspection mode is first selected and setting of inspection conditions is started. After a wafer to be inspected is designated, an inspection recipe is selected. After the designation of options such as transfer destination of inspection result data, the inspection start is instructed. After the inspection start instruction, wafer loading is started, calibration processing for an electron beam, alignment, calibration of luminance are automatically performed, and the inspection is performed.

After the inspection is terminated, the process proceeds to classification processing based upon a defect image. After the classification processing is terminated, an inspection result is outputted and the wafer is unloaded, thereby terminating the inspection.

Figure 6:
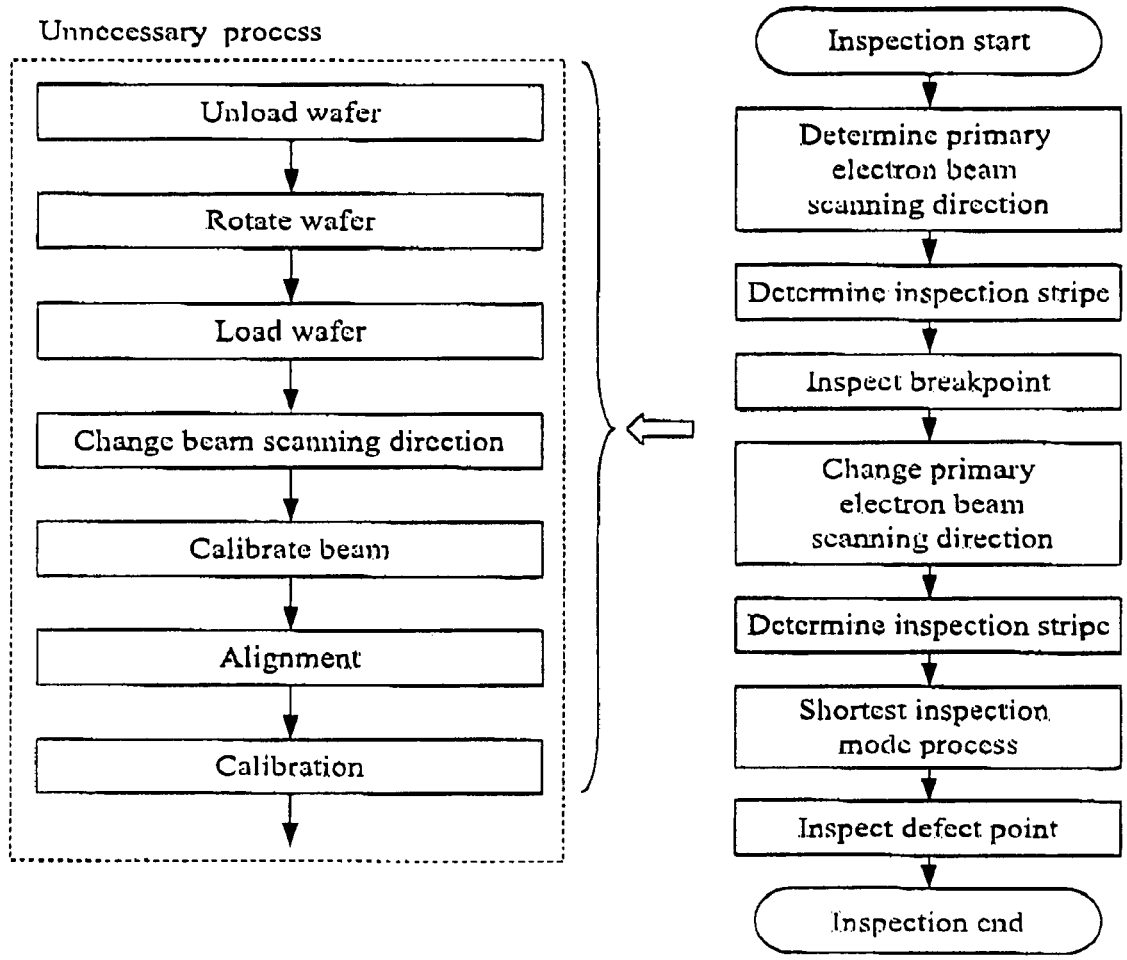
FIG. 6 is all explanatory diagram showing a detailed flow of the inspection according to the embodiment of the present invention.

Next, a detailed flow regarding the inspection of the present invention will be described with reference to FIG. 6.

In order to perform the inspection, a primary electron-beam scanning direction and an inspection stripe position are determined and the determined inspection stripe position is inspected. This breakpoint inspection performed first is called primary inspection.

Next, the primary electron-beam scanning direction and the inspection stripe position are determined based on the defect information obtained in the breakpoint inspection. Thereafter, the inspection stripe position is determined again based on information of the determined inspection stripe position and a shortest inspection mode designated by a user. Inspection is performed to the determined inspection stripe position. This defect point inspection performed second is called secondary inspection.

In a conventional technology, in order to perform the defect point inspection, wafer unloading is once performed to rotate a wafer, and then the wafer is loaded again. Since the wafer is unloaded once, it is necessary to perform calibration processing, alignment and luminance calibration of an electron beam again, and a large amount of time is required. In the embodiment of the present invention, since inspection can be performed continuously by changing the primary electron-beam scanning direction and a stage movement direction without loading and unloading wafers, efficient inspection can be realized.

An inspection example with respect to non-conduction due to insufficient etching and an etching gas reaction product and via chain conduction failure due to opening defect caused by plug opening blocking material which is a foreign material generated in the etching process will be described in detail with reference to FIG. 7 and subsequent drawings.

Figure 7:
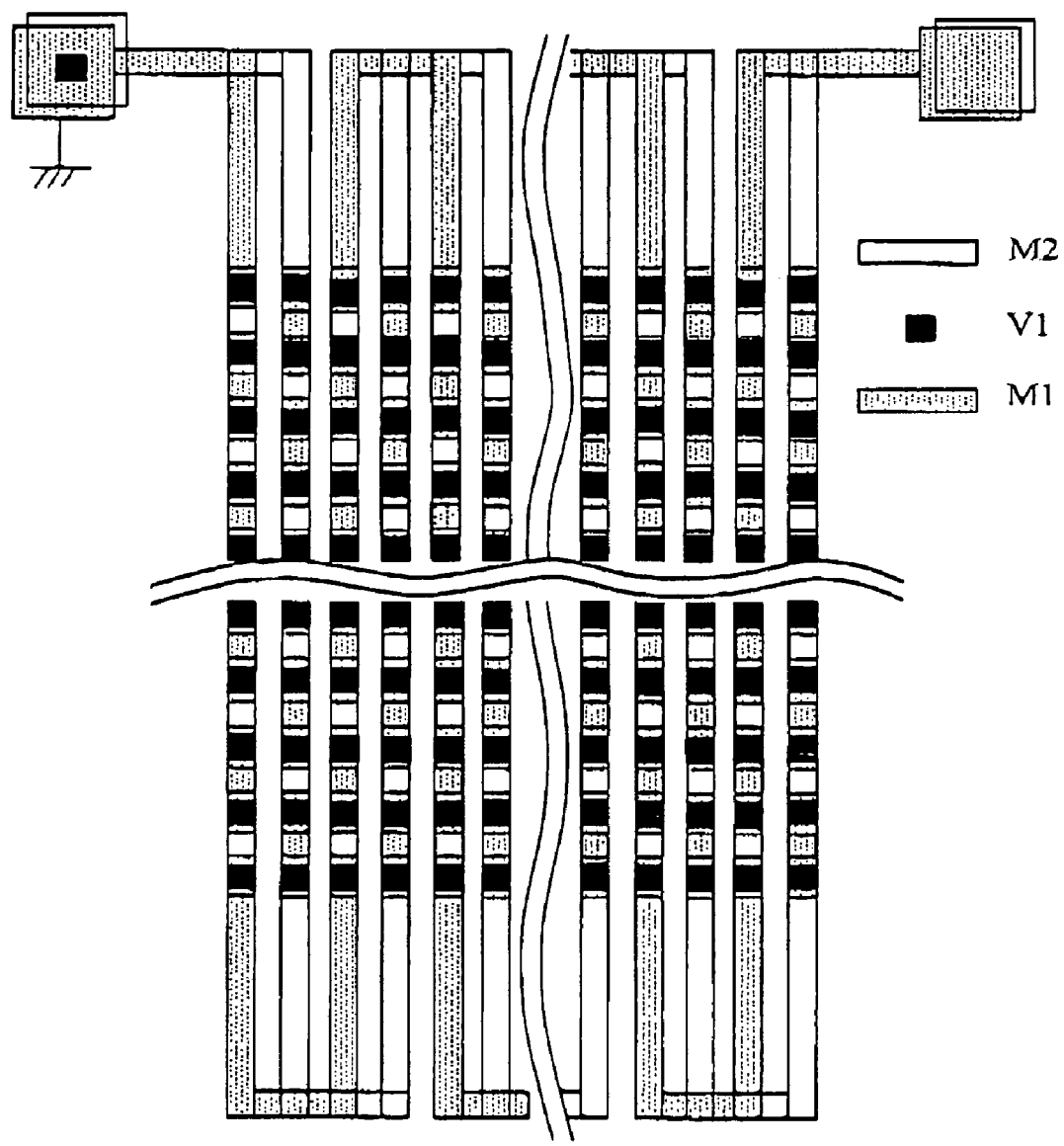
FIG. 7 is a view (plan view) showing a via chain structure according to the embodiment of the present invention.

FIG. 7 is a plan view showing a via chain structure. The via chain is composed of a first layer metal wire M1, a second layer metal wire M2 and a via V1 coupled with the first layer metal wire M1 and the second layer metal wire M2, and PADs are provided at both ends thereof.

Figure 8:
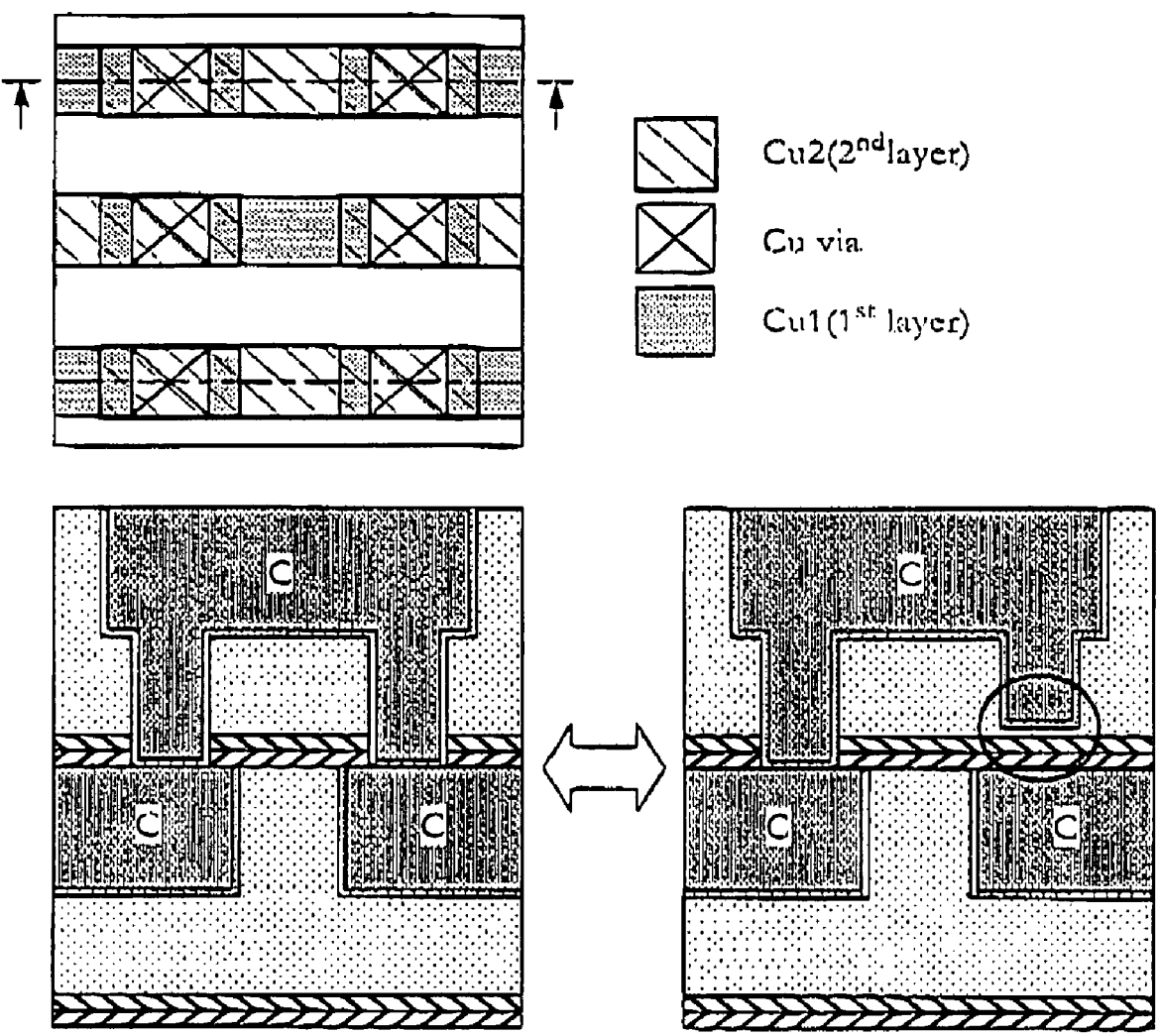
FIG. 8 is a view showing a non-conduction portion according to the embodiment of the present invention.

FIG. 8 shows an outline of non-conduction portion.

Figure 9:
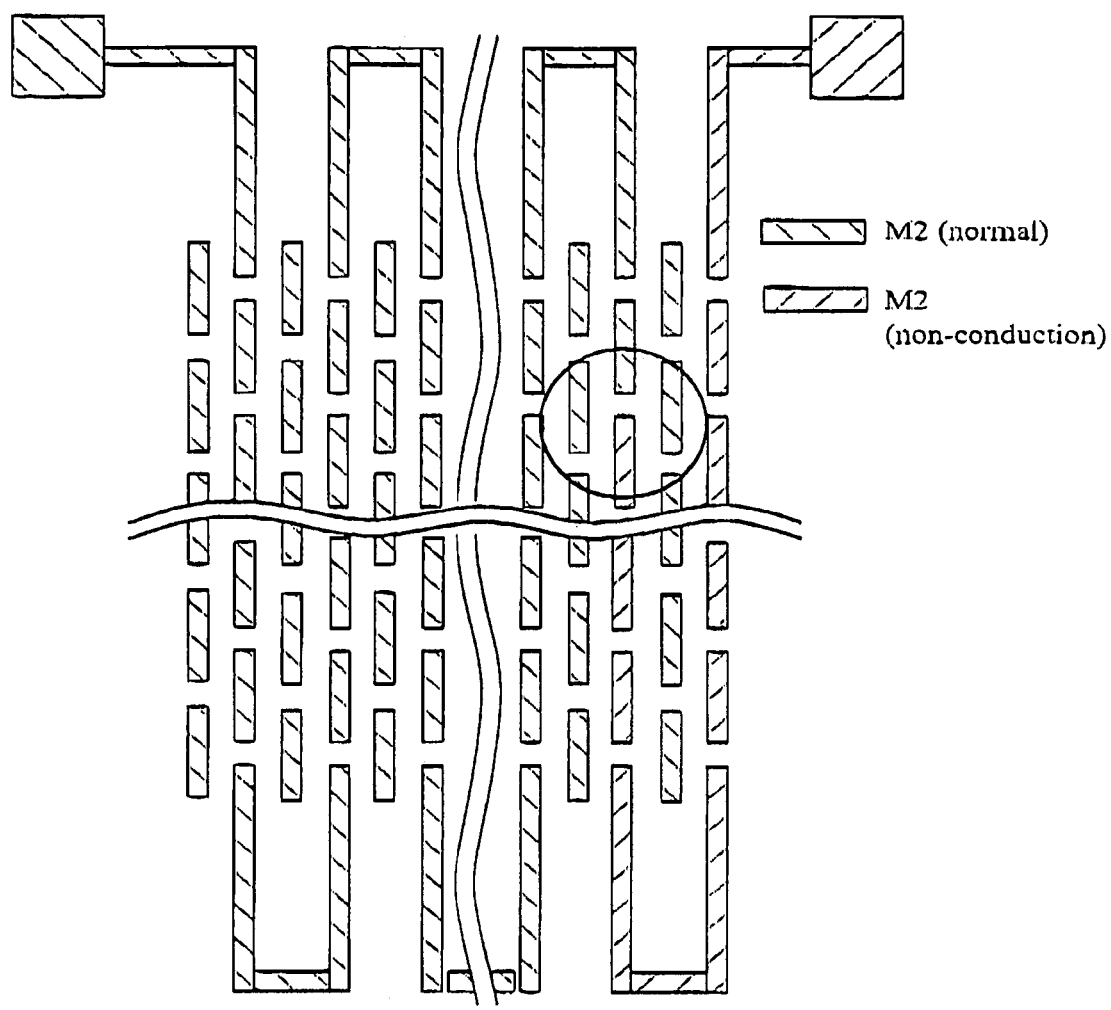
FIG. 9 is a view showing the via chain structure (at the time of generation of non-conduction) according to the embodiment of the present invention.

A sectional view at the lower left which is taken along the dotted line in the upper plan view shows a normal connection state, while a circled portion in a sectional view at the lower right shows a non-conduction state where the connection is failed. When a charged particle beam is emitted to the via chain having such a non-conduction defect, luminance of the wiring portion differs due to the difference in capacitance of the wires extending from the non-conduction portion forward and, backward. FIG. 9 is a plan view showing a via chain structure where the non-conduction occurs.

Figure 10:
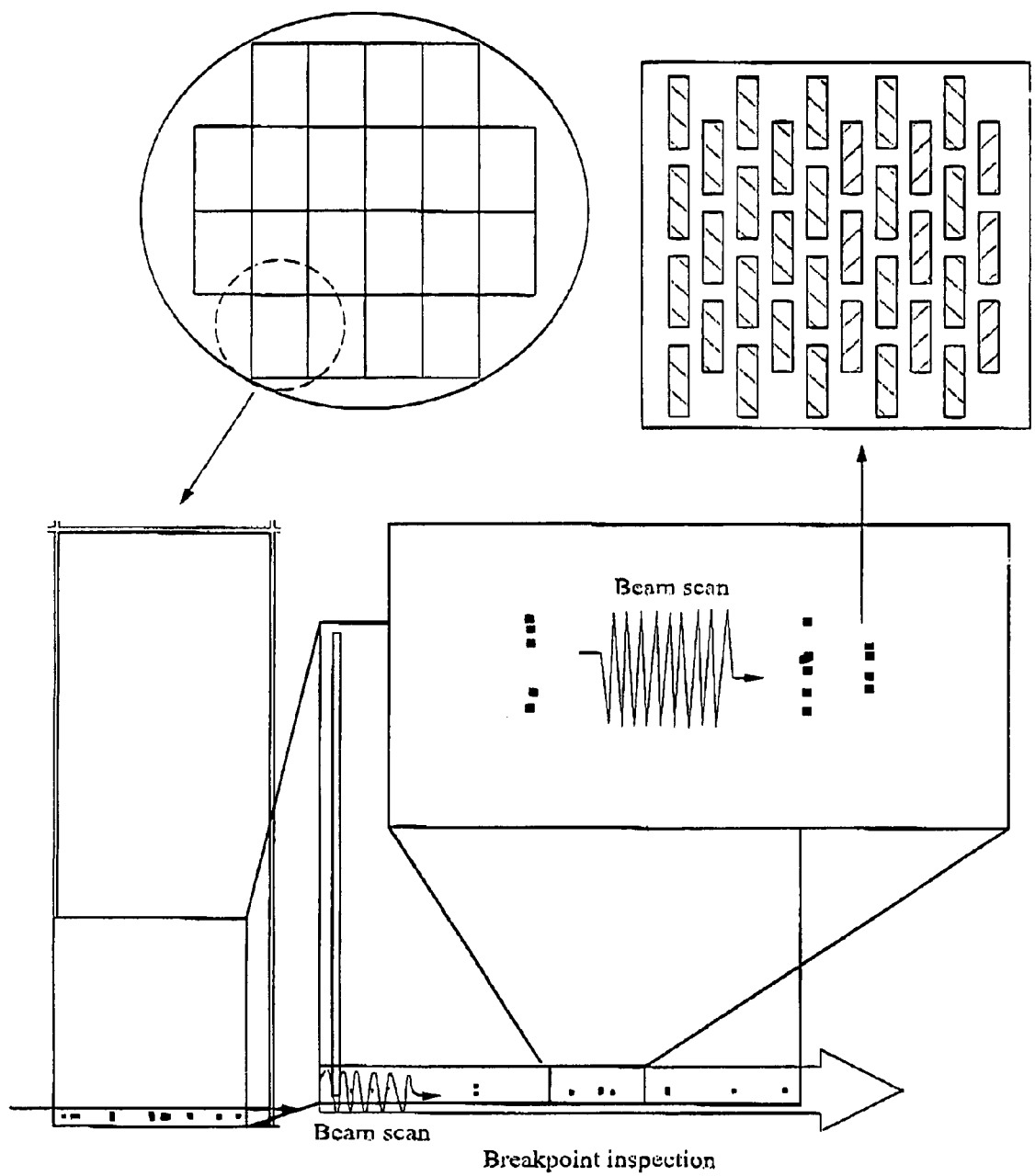
FIG. 10 is a diagram showing breakpoint inspection according to the embodiment of the present invention.

As shown in FIG. 10, difference in luminance of the wires is detected through the breakpoint inspection to specify the wire where a non-conduction defect is present.

Figure 11:
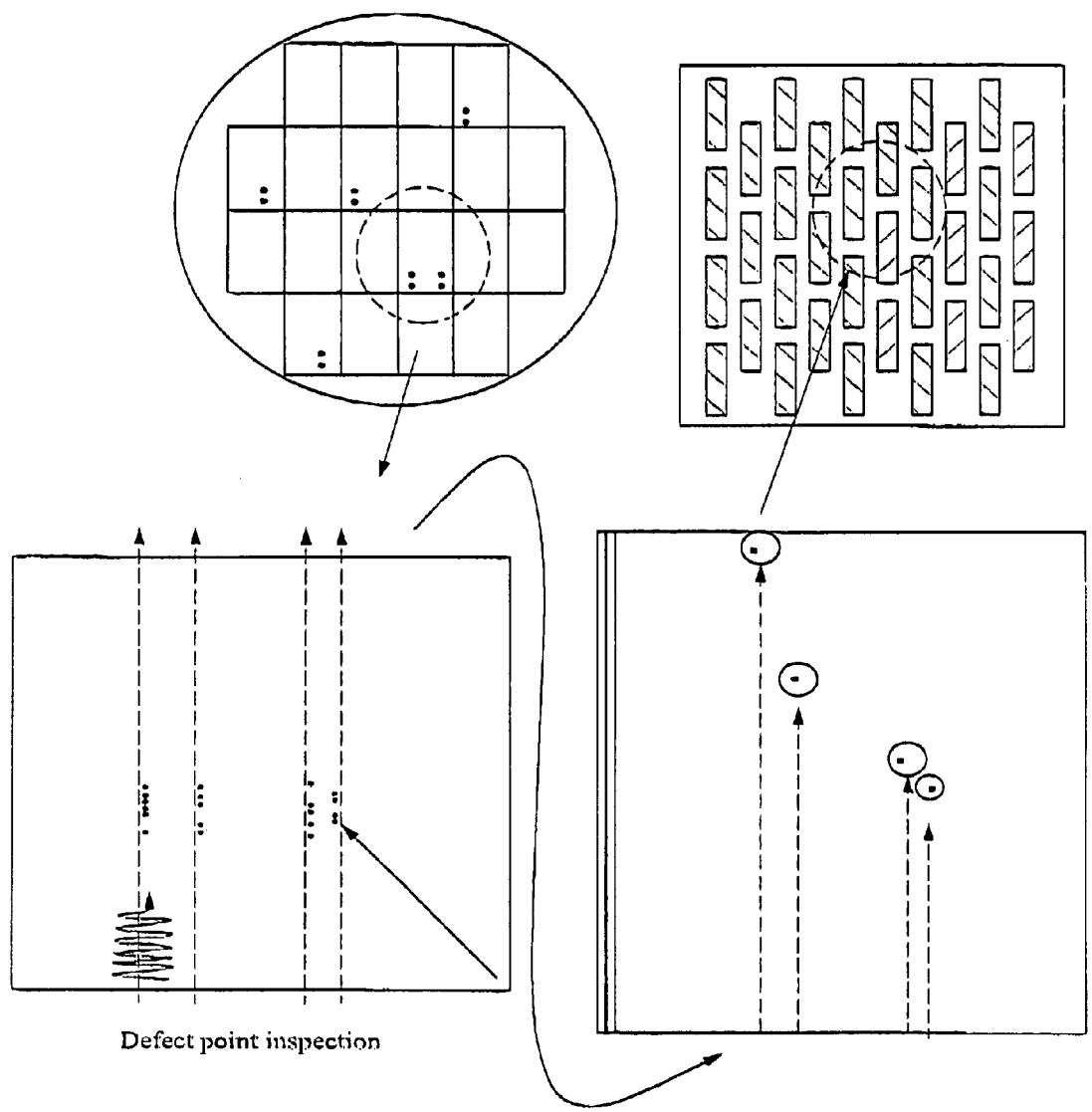
FIG. 11 is a diagram showing defect point inspection according to the embodiment of the present invention.

Thereafter, as shown in FIG. 11, a non-conduction position is specified by irradiating a charged particle beam in a direction orthogonal to the specified wire to perform the inspection. Since a wire where a defect is present is specified without inspecting the whole inspection region and the specified wire is further inspected in this manner, efficient inspection can be performed.

More specifically, in the primary inspection (breakpoint inspection) in which an irradiation beam is irradiated to the inspection wafer 104 to perform scanning, the stripe of the inspection region where a defect is present is determined by the comparison means and the determination means provided in the image processing circuit 46 and the control unit 5, and in the secondary inspection (defect point inspection), an irradiation beam is irradiated in a longitudinal direction of the determined stripe to perform scanning, and then a defect in the stripe is determined by the comparison means and the determination function of the determination means.

Therefore, inspection is performed rapidly compared with a conventional inspection where an irradiation beam is irradiated to the whole region of the inspection wafer 104 to perform scanning.

A method for determining an inspection stripe position will be described with reference to FIG. 12-1 to FIG. 12-3. When defects are detected in five dies as a result of a first breakpoint inspection, the five dies are set as inspection dies. A system 1 is called whole inspection region system, where the whole inspection region in the dies is inspected as an inspection region regardless of a defect position of the breakpoint inspection (FIG. 12-1).

Figures 2, 12:
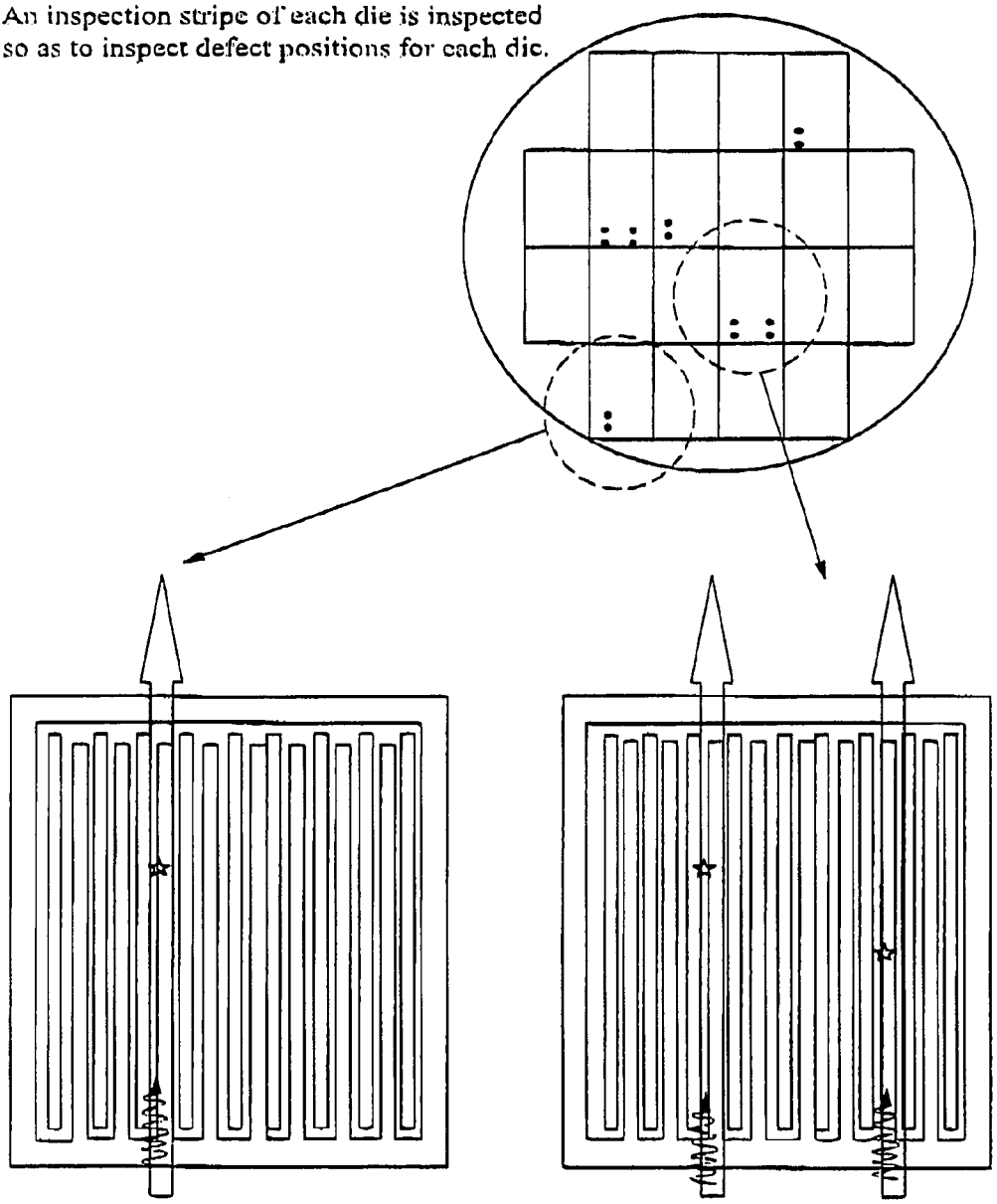
Figure 12:
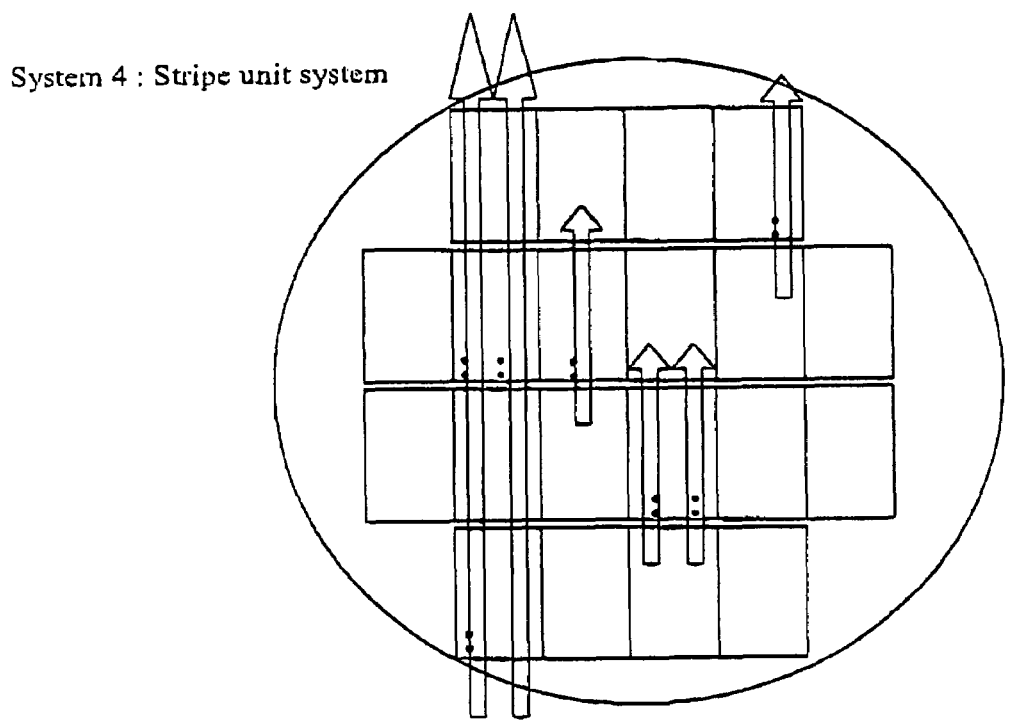
Figure 3:
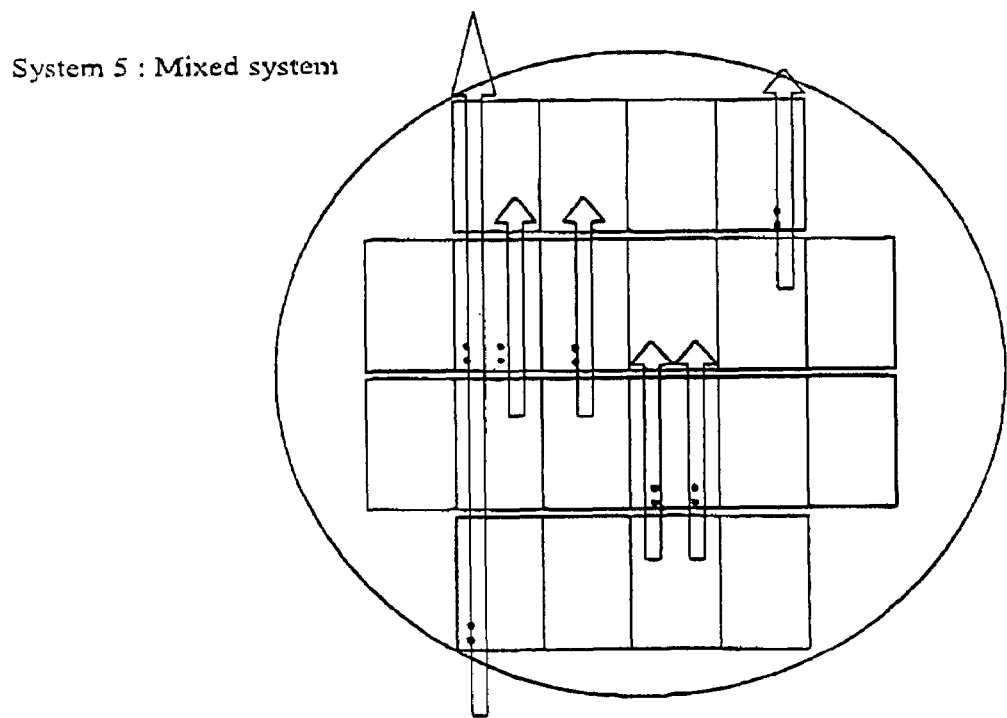

A system 2 is called all defect position system, where inspection is performed utilizing the inspection stripe for inspecting all defect positions detected in respective dies (FIG. 12-1). A system 3 is called die unit system, where each die is inspected individually utilizing inspection stripe for inspecting a defect position of each die (FIG. 12-2). A system 4 is called stripe unit system, where a stripe is determined so as to inspect a defect position which is present in a die in a stage movement direction (FIG. 12-3).

When defects are present at two portions in a die [1] and a defect is present at one portion in a die [2], two inspection stripes are used so as to inspect two defect positions of the die [1]. At this time, two inspection stripes are used for inspection in the die [2] though a defect is present at only one portion in the die [2].

A system 5 is called mixed system, where the inspection stripe is determined according to a combination of the stripe unit system and the die unit system (FIG. 12-3). A defect at one portion in each of the die [1] and the die [2] is inspected utilizing one inspection stripe, and the remaining defect of the die [1] is inspected utilizing an independent inspection stripe and the die [2] is not inspected.

A scanning order system of an inspection stripe determined as described above will be described with reference to FIG. 13-1 to FIG. 13-4.

Figure 13:
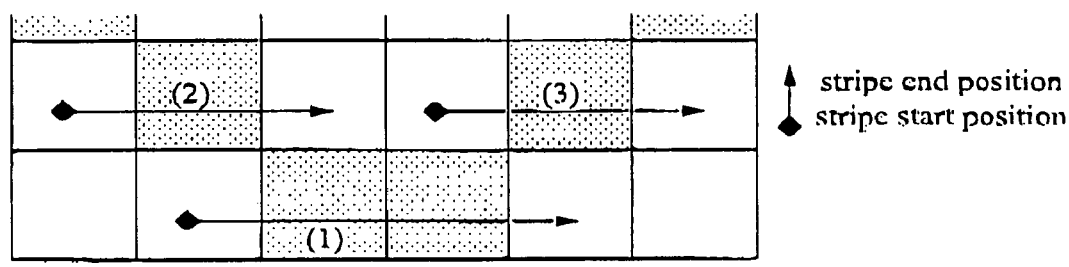
Figure 3:
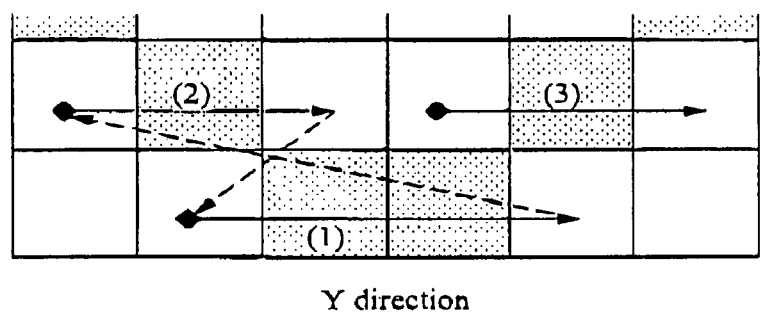

A system 1 is called standard sort system, where inspection is performed in series according to the arrangement order of dies shown below (FIG. 13-1).

(Inspection in X direction)

Inspection is performed from the stripe whose die Y number is closest to 0.

When die Y numbers are equal, the stripe whose die X number is closer to 0 has priority.

(Inspection in Y direction)

Inspection is performed from the stripe whose die X number is closest to 0.

When die X numbers are equal, the stripe whose die Y number is closer to 0 has priority.

A system 2 is called close sort system, where a movement distance from an end position of the inspection stripe at the lower portion of the wafer to a starting position of another inspection stripe is calculated and then a stripe having the shortest movement distance becomes a next stripe (FIG. 13-2).

A system 3 is called additional sort system, where addition of an inspection strip between the strips which minimizes the extension of movement distance between strips is confirmed, and inspection stripes are sequentially added to the positions where the extension of the movement distance can be minimized (FIG. 13-3, FIG. 13-4).

Further, when the wire size is smaller than a deflection width of the primary electron beam, the deflection width is reduced automatically and further high-speed inspection can be realized. For example, the deflection width can takes a value in a range of 31.4 nm to 150.0 nm according to the pixel size (FIG. 14-1).

Also, when a user inspection time is defined by an operation shown in FIG. 14-2, thinning of the inspection strips is performed according to the following three methods and the number of inspection strips is changed so that the inspection time falls in the defined time.

Method 1: filter/clustering

An inspection stripe is determined based on a defect remaining after the filtering according to defect shape/defect area or the like.

Method 2: ADC classification

An inspection stripe is determined only by a focused defect (specific classification code).

Method 3: sampling

Assuming that the number of determined inspection stripes is set to 100%, thinning of stripes is performed.

As described above, according to the embodiment, it is possible to provide a circuit pattern inspection method and apparatus for the same for detecting a defect at high speed by taking advantage of characteristics of a potential contrast method using a defect inspection structure and an electron beam defect detection apparatus which are presented in this specification or an inspection and analysis apparatus based upon them, thereby improving the capture efficiency of a critical electric defect and the search efficiency of a defective portion.

What is claimed is:

1. A circuit pattern inspection apparatus comprising:
   irradiation means for irradiating an irradiation beam of light, a laser beam or a charged particle beam to a surface of a substrate of a wafer on which a circuit pattern is formed;
   a control unit for setting a scanning direction of the irradiation beam and an inspection stripe position in a primary inspection;
   detection means for detecting a signal generated from the substrate by the irradiation beam;
   storage means for imaging the signal detected by the detection means to store the same;
   comparison means for comparing the stored image with an image formed from another equal circuit pattern; and
   determination means for determining stripes where a defect is present based on a result of the primary inspection,
   wherein the control unit controls a deflector and a stage in a secondary inspection such that the irradiation beam is scanned along a longitudinal direction of the determined stripe and then the determination means determines the defect position in said determined stripe from the result of the secondary inspection.

2. The circuit pattern inspection apparatus according to claim 1,
   wherein, based on defect data detected in the primary inspection, an inspection region for the secondary inspection is calculated to perform the secondary inspection.

3. The circuit pattern inspection apparatus according to claim 1,
   wherein, based on defect data detected in the primary inspection, a stage moving method is changed so as to minimize an inspection time for the secondary inspection.

4. The circuit pattern inspection apparatus according to claim 1,
   wherein, based on defect data detected in the primary inspection, a deflection region of a charged particle beam in the secondary inspection is changed.

5. The circuit pattern inspection apparatus according to claim 1,
   wherein, after unnecessary defect data is eliminated from defect data detected in the primary inspection, an inspection region of the secondary inspection is calculated to perform the secondary inspection.

6. The circuit pattern inspection apparatus according to claim 1,
   wherein, after unnecessary defect data is eliminated from defect data detected in the primary inspection, a stage moving method is changed so as to minimize an inspection time for the secondary inspection.

7. The circuit pattern inspection apparatus according to claim 1,
   wherein, after unnecessary defect data is eliminated from defect data detected in the primary inspection, a deflection region of a charged particle beam in the secondary inspection is calculated to perform the secondary inspection.

8. The circuit pattern inspection apparatus according to claim 1,
   wherein, when an inspection region and a deflection region of a charged particle beam in the secondary inspection are calculated based on defect data detected in the primary inspection, the inspection region and the deflection region are determined from an upper limit value of an inspection time.

9. A circuit pattern inspection apparatus comprising:
   irradiation means for irradiating an irradiation beam of light, a laser beam or a charged particle beam to a surface of a substrate of a wafer on which a circuit pattern is formed;
   a stage on which said wafer is placed for moving the wafer in an arbitrary direction;
   stage control means for controlling movement of said stage;
   detection means for detecting a signal generated from said substrate by said irradiation beam;
   storage means for imaging the signal detected by said detection means to store the image;
   comparison means for comparing said stored image with an image formed from another equal circuit pattern; and
   determination means for determining a defect on said circuit pattern from the comparison result,
   wherein a determination function to determine a defect through a primary inspection, where the stripe including a defect is determined by the irradiation and the scanning of the irradiation beam and a secondary inspection where said irradiation beam is scanned along a longitudinal direction of the determined stripe in order to specify the defect position in the determined stripe is provided.

10. The circuit pattern inspection apparatus according to claim 9,
    wherein an irradiation and scanning direction in said primary inspection intersects the longitudinal direction of said stripe.

11. The circuit pattern inspection apparatus according to claim 9,
    wherein, based on defect data detected in said primary inspection, said stripe to be inspected next is calculated.

12. The circuit pattern inspection apparatus according to claim 9,
    wherein, based on defect data detected in said primary inspection, a stage moving method is changed so as to minimize an inspection time for said secondary inspection.

13. The circuit pattern inspection apparatus according to claim 9,
    wherein said irradiation beam in said primary inspection or said secondary inspection has a deflection region which swings right and left with respect to an irradiation and scanning direction.

14. The circuit pattern inspection apparatus according to claim 13, wherein, based on defect data detected in said primary inspection, said irradiation beam changes a width of a deflection region of the irradiation beam in said secondary inspection.

15. The circuit pattern inspection apparatus according to claim 9,
wherein unnecessary defect data is eliminated from defect data detected in said primary inspection, and the inspection region in said secondary inspection is calculated based on remaining defect data.

16. The circuit pattern inspection apparatus according to claim 9,
wherein unnecessary defect data is eliminated from defect data detected in said primary inspection, and a stage moving method is changed so as to minimize an inspection time for said secondary inspection based on remaining defect data.

17. The circuit pattern inspection apparatus according to claim 9,
wherein unnecessary defect data is eliminated from defect data detected in said primary inspection, and a deflection region of said irradiation beam is calculated based on remaining defect data to perform the inspection.

18. The circuit pattern inspection apparatus according to claim 9,
wherein, when an inspection region and a deflection region of said irradiation beam in said secondary inspection are calculated based on defect data detected in a first inspection, the inspection region and the deflection region are determined from an upper limit value of an inspection time.

* * * * *